US010377798B2

(12) United States Patent
Khurana et al.

(10) Patent No.: US 10,377,798 B2
(45) Date of Patent: Aug. 13, 2019

(54) RECOMBINANT RESPIRATORY SYNCYTIAL VIRUS G PROTEIN FRAGMENTS

(71) Applicant: The United States of America as Represented by the Secretary of the Department of Health and Human Services, Bethesda, MD (US)

(72) Inventors: Surender Khurana, Clarksburg, MD (US); Hana Golding, Rockville, MD (US)

(73) Assignee: The United States of America, as rerpresented by the Secretary, Department of Health and Human Services, Bethesda, MD (US)

( * ) Notice: Subject to any disclaimer, the term of this patent is extended or adjusted under 35 U.S.C. 154(b) by 143 days.

(21) Appl. No.: 15/100,914

(22) PCT Filed: Dec. 2, 2014

(86) PCT No.: PCT/US2014/068144

§ 371 (c)(1),
(2) Date: Jun. 1, 2016

(87) PCT Pub. No.: WO2015/084838

PCT Pub. Date: Jun. 11, 2015

(65) Prior Publication Data

US 2016/0304565 A1 Oct. 20, 2016

Related U.S. Application Data

(60) Provisional application No. 61/910,623, filed on Dec. 2, 2013.

(51) Int. Cl.

| | |
|---|---|
| ***C07K 14/005*** | (2006.01) |
| ***A61K 39/155*** | (2006.01) |
| ***C07K 14/05*** | (2006.01) |
| ***C07K 16/10*** | (2006.01) |
| ***C12N 7/00*** | (2006.01) |
| *A61K 39/00* | (2006.01) |

(52) U.S. Cl.

CPC .......... *C07K 14/005* (2013.01); *A61K 39/155* (2013.01); *C07K 14/05* (2013.01); *C07K 16/1027* (2013.01); *C12N 7/00* (2013.01); *A61K 2039/525* (2013.01); *A61K 2039/53* (2013.01); *A61K 2039/575* (2013.01); *C07K 2317/76* (2013.01); *C07K 2319/21* (2013.01); *C07K 2319/50* (2013.01); *C12N 2760/18522* (2013.01); *C12N 2760/18534* (2013.01); *C12N 2760/18571* (2013.01)

(58) Field of Classification Search

None

See application file for complete search history.

(56) References Cited

U.S. PATENT DOCUMENTS

| | | | | |
|---|---|---|---|---|
| 6,309,649 B1 * | 10/2001 | Cates | A61K 39/155 | 424/211.1 |
| 2005/0158712 A1 * | 7/2005 | Leboulch | A61K 48/0091 | 435/5 |
| 2014/0363460 A1 * | 12/2014 | Wang | A61K 39/12 | 424/186.1 |

FOREIGN PATENT DOCUMENTS

| | | |
|---|---|---|
| WO | 2010/075491 A2 | 7/2010 |
| WO | WO 2010/075491 * | 7/2010 |
| WO | 2013/116965 A1 | 8/2013 |

OTHER PUBLICATIONS

Percent identity to SEQ #2 of U.S. Appl. No. 15/100,914 (dated 2018).*

Wang, et al., "A New Positive/Negative Selection Scheme for Precise BAC Recombineering," *Mol Biotechnol*, vol. 42, pp. 110-116 (2009).

International Search Report for International Application No. PCT/US2014/068144 dated Feb. 27, 2015.

Anderson et al., Strategic priorities for respiratory syncytial virus (RSV) vaccine development, *Vaccine*, 31S, B209-B215, Apr. 2013.

Fuentes et al., Preclinical evaluation of bacterially produced RSV-G protein vaccine: Strong protection against RSV challenge in cotton rat model, *Scientific Reports*, 7:42428, 2017.

Fuentes et al., Nonglycosylated G-Protein Vaccine Protects against Homologous and Heterologous Respiratory Syncytial Virus (RSV) Challenge, while Glycosylated G Enhances RSV Lung Pathology and Cytokine Levels, *Journal of Virology*, 89(16), 2015.

Hancock et al., Immune Responses to the Nonglycosylated Ectodomain of Respiratory Syncytial Virus Attachment Glycoprotein Mediate Pulmonary Eosinophilia in Inbred Strains of Mice with Different MHC Haplotypes, *Journal of Medical Virology*, 70:301-308, 2003.

Ongarora et al., "Phthalocyanme-peptide conjugates for epidermal growth factor receptor targeting." *Journal of Medicinal Chemistry* 55, No. 8 (2012): 3725-3738.

* cited by examiner

*Primary Examiner* — Shanon A. Foley
*Assistant Examiner* — Myron G Hill
(74) *Attorney, Agent, or Firm* — Klarquist Sparkman, LLP

(57) ABSTRACT

Compositions and methods useful for producing an immune response in a subject specific for the RSV G protein are described herein. The new methods and compositions described herein are made possible by the development of a new recombinant RSV G protein fragment, which has been engineered for in vitro production and is antigenically similar to the native RSV G protein. The recombinant RSV G protein fragment is capable of inducing the production of RSV G-specific antibodies when injected into a subject. These antibodies can recognize both RSV A and RSV B strains and inhibit infection of both viruses. Accordingly, the compositions and methods described herein may be useful in protecting subjects from RSV infection via immunization, raising antibodies specific for RSV, which can in turn be used to treat RSV infection.

18 Claims, 20 Drawing Sheets

Specification includes a Sequence Listing.

```
                                        1                                                50
SEQ ID NO: 4  RSV_A_ST_A2        (1)   MSKNKDQRTAKTLERTWDTLNHLLFISSCLYKLNLKSVAQITLSILAMII
SEQ ID NO: 5  RSV_A_ST_LONG      (1)   MSKNKDQRTAKTLEKTWDTLNHLLFISSGLYKLNLKSIAQITLSILAMII
SEQ ID NO:6   RSV_B_ST_18537     (1)   MSKHKNQRTARTLEKTWDTLNHLIVISSCLYRLNLKSIAQIALSVLAMII
SEQ ID NO: 7  RSV_B_ST_B1        (1)   MSKHKNQRTARTLEKTWDTLNHLIVISSCLYRLNLKSIAQIALSVLAMII

                                        51                                              100
              RSV_A_ST_A2       (51)   STSLIIAAIIFIASANHKVTPTTAIIQDATSQIKNTTPTYLTQNPQLGIS
              RSV_A_ST_LONG     (51)   STSLIITAIIFIASANHKVTLTTAIIQDATSQIKNTTPTYLTQDPQLGIS
              RSV_B_ST_18537    (51)   STSLIIAAIIFIISANHKVTLTTVTVQTIKNHTEKNISTYLTQVPPERVN
              RSV_B_ST_B1       (51)   STSLIIAAIIFIISANHKVTLTTVTVQTIKNHTEKNITTYLTQVPPERVS

                                        101                                             150
              RSV_A_ST_A2      (101)   PSNPSEITSQITTILASTTPGVKSTLQSTTVKTKNTTTTQTQPSKPTTKQ
              RSV_A_ST_LONG    (101)   FSNLSEITSQTTTILASTTPGVKSNLQPTTVKTKNTTTTQTQPSKPTTKQ
              RSV_B_ST_18537   (101)   SSKQPTTTSPIHTNSATISPNTKSETHHTTAQTKGRITTSTQTNKPSTKS
              RSV_B_ST_B1      (101)   SSKQPTTTSPIHTNSATTSPNTKSETHHTTAQTKGRTTTSTQTNKPSTKP

                                        151                                             200
              RSV_A_ST_A2      (151)   RQNKPPSKPNNDFHFEVFNFVPCSICSNNPTCWAICKRIPNKKPGKKTTT
              RSV_A_ST_LONG    (151)   RQNKPPNKPNNDFHFEVFNFVPCSICSNNPTCWAICKRIPNKKPGKKTTT
              RSV_B_ST_18537   (151)   RSKNPPKKPKDDYHFEVFNFVPCSICGNNQLCKSICKTIPSNKPKKKPTI
              RSV_B_ST_B1      (151)   RLKNPPKKPKDDYHFEVFNFVPCSICGNNQLCKSICKTIPSNKPKKKPTI

                                        201                                             250
              RSV_A_ST_A2      (201)   KPTKKPTLKTT-KKDPKPQTTKSKEVPTTKPTEEPTINTTKTNIITTLLT
              RSV_A_ST_LONG    (201)   KPTKKPTFKTT-KKDHKPQTTKPKEVPTTKPTEEPTINTTKTNIITTLLT
              RSV_B_ST_18537   (201)   KPTNKPTTKTTNKRDPKTPAKMPKKEIITNPAKKPTLKTTERDTSISQST
              RSV_B_ST_B1      (201)   KPTNKPTTKTTNKRDPKTPAKTTKKETTTNPTKKPTLTTTERDTSTSQST

                                        251                                            299
              RSV_A_ST_A2      (250)   SNTTGNPELTSQMETFHSTSSEGNPSPSQVSTTSEYPSQPSSPPNTPRQ
              RSV_A_ST_LONG    (250)   NNTTGNPKLTSQMETFHSTSSEGNLSPSQVSTTSEHPSQPSSPPNTTRQ
              RSV_B_ST_18537   (251)   VLDTITPKYTIQQQSLHSTTSENTPSSTQIPTASEPSTLNPN-------
              RSV_B_ST_B1      (251)   VLDTTTLEHTIQQQSLHSTTPENTPNSTQTPTASEPSTSNSTQNTQSHA
```

Fig. 1

| | | RSV-PRNT | |
|---|---|---|---|
| | | A2 | B1 |
| Controls | Pre-Vac | <40 | <40 |
| REG | IM1 | <40 | <40 |
| | IM2 | 12486 | 1468 |
| | IM3 | 31611 | 2178 |
| | IM4 | 12221 | 458 |
| RMG | IM1 | 138 | <40 |
| | IM2 | 161 | <40 |
| | IM3 | 17348 | 1985 |
| | IM4 | 5271 | 523 |
| | IM5 | 4532 | 234 |

Fig. 9

Fig. 14
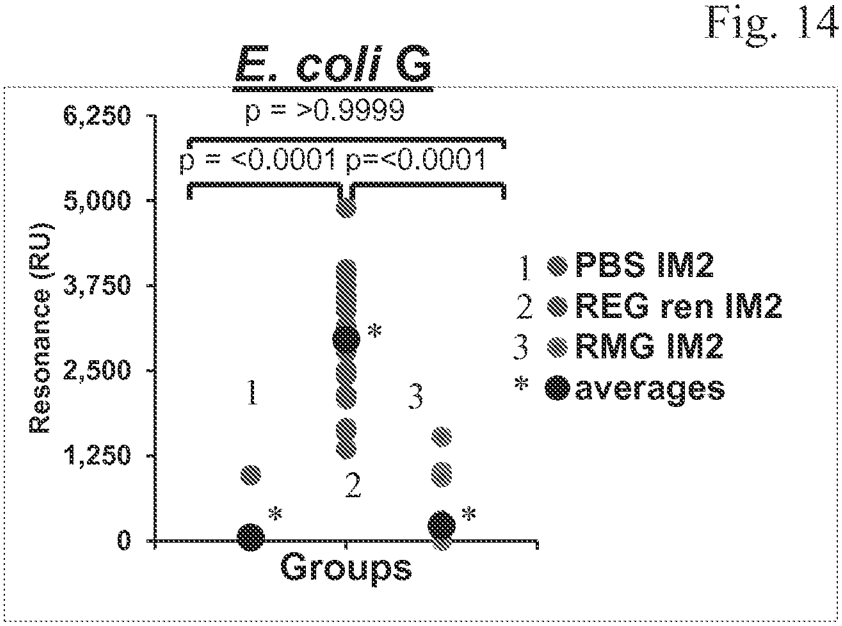
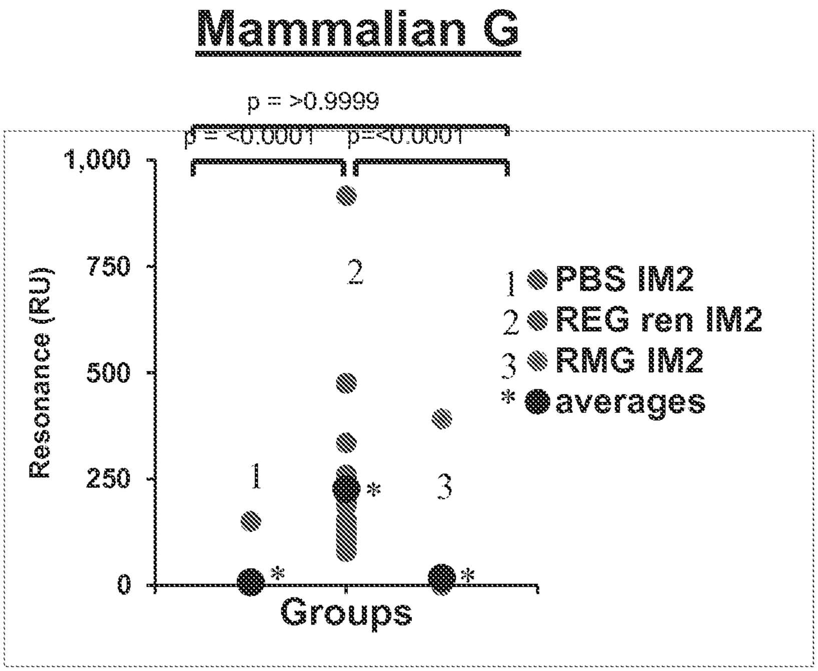

| | | PBS | REG | RMG |
|---|---|---|---|---|
| Th1 cytokines | IL-1a | 39.46 ± 1.50 | 63.77 ± 15.70$^{*}$ | 99.71 ± 10.76$^{*\#}$ |
| | IL-1b | 460.95 ± 61.36 | 499.99 ± 108.97 | 1341.63 ± 396.63$^{*\#}$ |
| | IL-2 | 33.07 ± 1.86 | 36.06 ± 6.22 | 57.91 ± 6.27$^{*\#}$ |
| | IL-12p40 | 105.52 ± 3.40 | 212.82 ± 109.13 | 93.97 ± 69.25 |
| | IL-12p70 | 96.64 ± 14.02 | 137.21 ± 37.08 | 308.91 ± 88.60$^{*\#}$ |
| | GM-CSF | 300.06 ± 20.84 | 292.35 ± 24.43 | 336.40 ± 25.04$^{\#}$ |
| | IFN-g | 18.96 ± 1.83 | 25.48 ± 6.37 | 46.22 ± 4.33$^{*\#}$ |
| | TNF-a | 328.87 ± 31.03 | 374.53 ± 42.91 | 644.31 ± 60.47$^{*\#}$ |
| Th2 cytokines | IL-4 | 1 ± 0 | 3.11 ± 3.68 | 451 ± 223.96$^{*\#}$ |
| | IL-5 | 5.82 ± 1.62 | 9.83 ± 3.74 | 176.67 ± 72.08$^{*\#}$ |
| | IL-6 | 8.1 ± 1.80 | 11.92 ± 14.14 | 64.44 ± 20.06$^{*\#}$ |
| | IL-9 | 199.42 ± 34.23 | 95.41 ± 43.94 | 356.9 ± 268.40$^{\#}$ |
| | IL-13 | 260.81 ± 106.76 | 267.51 ± 56.78 | 581.69 ± 55.35$^{*\#}$ |
| Th17 cytokines | IL-17 | 9.94 ± 0.84 | 11.36 ± 2.93 | 13.45 ± 3.17 |
| Chemokines and Growth Factors | Eotaxin | 1018.32 ± 143.14 | 1065.05 ± 132.29 | 1413.19 ± 162.62$^{*\#}$ |
| | G-CSF | 40.35 ± 8.87 | 139.19 ± 158.40 | 136.7 ± 65.89 |
| | KC | 196.76 ± 48.80 | 307.05 ± 174.47 | 564.91 ± 130.99$^{*\#}$ |
| | MCP-1 | 381.98 ± 32.60 | 626.59 ± 431.41 | 2474.1 ± 1153.93$^{*\#}$ |
| | MIP-1a | 50.98 ± 4.27 | 63.21 ± 23.06 | 2025.14 ± 1767.41$^{*\#}$ |
| | MIP-1b | 59.54 ± 7.74 | 64.41 ± 11.47 | 289.51 ± 155.53$^{*\#}$ |
| | RANTES | 272.79 ± 7.69 | 436.25 ± 194.68 | 711.81 ± 227.38$^{*}$ |
| Th1 + Th2 expressed cytokines | IL-3 | 11.72 ± 0.84 | 14.19 ± 2.72 | 13.65 ± 2.22 |
| | IL-10 | 48.7 ± 4.12 | 61.12 ± 16.27 | 148.83 ± 16.42$^{*\#}$ |

| | | PBS | REG | RMG |
|---|---|---|---|---|
| Th1 cytokines | IL-1a | 44.92 ± 0.74 | 74.67 ± 28.83 | 72.63 ± 31.61 |
| | IL-1b | 382.4 ± 31.23 | 458.09 ± 163.23 | 555.17 ± 169.00 |
| | IL-2 | 45.42 ± 1.27 | 33.59 ± 6.84 | 41.99 ± 5.59 |
| | IL-12p40 | 126.84 ± 10.35 | 350.63 ± 280.77 | 137.23 ± 16.33 |
| | IL-12p70 | 225.26 ± 18.19 | 107.43 ± 36.64* | 164.34 ± 18.41# |
| | GM-CSF | 267.88 ± 23.36 | 243.28 ± 54.17 | 318.15 ± 27.24# |
| | IFN-g | 28.8 ± 0 | 22.24 ± 7.65 | 38.26 ± 4.79# |
| | TNF-a | 361.28 ± 25.12 | 332.51 ± 137.06 | 556.09 ± 51.82# |
| Th2 cytokines | IL-4 | 1 ± 0 | 5.94 ± 7.69 | 192.64 ± 186.95 |
| | IL-5 | 7.58 ± 0.99 | 8.66 ± 4.34 | 23.12 ± 3.75*# |
| | IL-6 | 0.6 ± 0.57 | 8.99± 12.92 | 18.35 ± 10.17 |
| | IL-9 | 165.86 ± 14.79 | 10 ± 0 | 947.08 ± 544.62# |
| | IL-13 | 393.06 ± 7.21 | 281.75 ± 94.86 | 399.33 ± 101.67 |
| Th17 cytokines | IL-17 | 16.16 ± 0.79 | 10.59 ± 2.14 | 9.01 ± 1.180 |
| Chemokines and Growth Factors | Eotaxin | 1066.54 ± 8.63 | 916.13 ± 108.81 | 1157.54 ± 106.41# |
| | G-CSF | 48.26 ± 2.06 | 95.14 ± 96.90 | 53.11 ± 31.50 |
| | KC | 76.46 ± 2.52 | 177.95 ± 93.03 | 198.47 ± 83.40 |
| | MCP-1 | 209.04 ± 23.42 | 477.73 ± 288.94 | 493.49 ± 243.03 |
| | MIP-1a | 41.42 ± 3.25 | 66.31 ± 28.76 | 272.33 ± 179.49# |
| | MIP-1b | 63.78 ± 2.63 | 61.01 ± 11.26 | 95.16 ± 25.99# |
| | RANTES | 333.42 ± 8.46 | 713.51 ± 315.15 | 453.95 ± 130.01 |
| Th1 + Th2 expressed cytokines | IL-3 | 17.7 ± 0.93 | 11.37 ± 2.25* | 11.11 ± 1.81* |
| | IL-10 | 91.64 ± 9.67 | 62.79 ± 17.07 | 88.24 ± 20.68 |

| | Immunization | Perivasculiitis | Bronchitis Bronchiolitis | Int. pneumonia | Septal necrosis | Pleuritis | Total 20 max |
|---|---|---|---|---|---|---|---|
| | PBS | 0 | 1 | 0 | 1 | 0 | 2 |
| | REG | 0 | 0.3 | 0 | 0.3 | 0 | 0.7 |
| RSV A2 | RMG | 2 | 1 | 0.7 | 0 | 0 | 3.7 |
| | PBS | 1 | 1 | 1.5 | 0 | 0 | 3.5 |
| | REG | 0.3 | 0.3 | 0 | 0 | 0 | 0.6 |
| RSV B1 | RMG | 2 | 2 | 0 | 1.3 | 0 | 5.3 |

| | | REG | RMG |
|---|---|---|---|
| *Neutralizing Antibodies* | *A2* | *Yes* | *No* |
| | *B1* | *No* | *No* |
| *Protection* | *A2* | *Yes* | *Partial* |
| | *B1* | *Yes* | *Partial* |
| *Cytokine levels* | *A2* | *Comparable to placebo* | *High levels of Th1, Th2 and chemokines* |
| | *B1* | *Comparable to placebo* | *High levels of Th1, Th2 and chemokines* |
| *Pathology* | *A2* | *Lower than to placebo* | *Higher than placebo* |
| | *B1* | *Lower than to placebo* | *Higher than placebo* |

Fig. 18

SEQUENCE LISTING

```
<160> NUMBER OF SEQ ID NOS: 9

<210> SEQ ID NO 1
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1

cataaagtca ccccgaccac ggcgattatc caggatgcca cctctcaaat caaaaacacc     60

acgccgacgt acctgaccca gaatccgcaa ctgggcattt caccgtcgaa cccgtcagaa    120

atcacctcgc agattaccac gatcctggca agcaccacgc cgggtgtcaa aagcacgctg    180

caatctacca cggtgaaaac caaaaatacc acgaccacgc agacccaacc gagcaaaccg    240

accacgaaac agcgtcaaaa taaaccgccg tctaaaccga acaatgattt tcacttcgaa    300

gtgtttaact tcgttccgtg cagtatttgt tccaacaatc cgacctgctg ggccatttgt    360

aaacgcatcc cgaacaaaaa accgggcaag aaaaccacga ccaaaccgac gaaaaaaccg    420

accctgaaaa cgaccaaaaa agacccgaaa ccgcagacga ccaaaagcaa agaagtgccg    480

acgaccaaac cgacggaaga accgaccatt aacacgacca aaaccaatat tatcacgacc    540
```

ctgctgacct ccaacacgac cggcaatccg gaactgacct cacagatgga aacgttccat 600
tcgaccagct ctgaaggtaa tccgagcccg tctcaggtca gcacgacctc cgaatacccg 660
agccagccgt cttctccgcc gaataccccg cgtcag 696

<210> SEQ ID NO 2
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

His Lys Val Thr Pro Thr Thr Ala Ile Ile Gln Asp Ala Thr Ser Gln
1 5 10 15

Ile Lys Asn Thr Thr Pro Thr Tyr Leu Thr Gln Asn Pro Gln Leu Gly
20 25 30

Ile Ser Pro Ser Asn Pro Ser Glu Ile Thr Ser Gln Ile Thr Thr Ile
35 40 45

Leu Ala Ser Thr Thr Pro Gly Val Lys Ser Thr Leu Gln Ser Thr Thr
50 55 60

Val Lys Thr Lys Asn Thr Thr Thr Thr Gln Thr Gln Pro Ser Lys Pro
65 70 75 80

Thr Thr Lys Gln Arg Gln Asn Lys Pro Pro Ser Lys Pro Asn Asn Asp
85 90 95

Phe His Phe Glu Val Phe Asn Phe Val Pro Cys Ser Ile Cys Ser Asn
100 105 110

Asn Pro Thr Cys Trp Ala Ile Cys Lys Arg Ile Pro Asn Lys Lys Pro
115 120 125

Gly Lys Lys Thr Thr Thr Lys Pro Thr Lys Lys Pro Thr Leu Lys Thr
130 135 140

Thr Lys Lys Asp Pro Lys Pro Gln Thr Thr Lys Ser Lys Glu Val Pro
145 150 155 160

Thr Thr Lys Pro Thr Glu Glu Pro Thr Ile Asn Thr Thr Lys Thr Asn
165 170 175

Ile Ile Thr Thr Leu Leu Thr Ser Asn Thr Thr Gly Asn Pro Glu Leu
180 185 190

Thr Ser Gln Met Glu Thr Phe His Ser Thr Ser Ser Glu Gly Asn Pro
195 200 205

Ser Pro Ser Gln Val Ser Thr Thr Ser Glu Tyr Pro Ser Gln Pro Ser
210 215 220

Ser Pro Pro Asn Thr Pro Arg Gln
225 230

<210> SEQ ID NO 3
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3
cacaaagtca caccaacaac tgcaatcata caagatgcaa caagccagat caagaacaca 60
accccaacat acctcaccca gaatcctcag cttggaatca gtccctctaa tccgtctgaa 120

```
attacatcac aaatcaccac catactagct tcaacaacac caggagtcaa gtcaaccctg    180

caatccacaa cagtcaagac caaaaacaca acaacaactc aaacacaacc cagcaagccc    240

accacaaaac aacgccaaaa caaaccacca agcaaaccca ataatgattt tcactttgaa    300

gtgttcaact ttgtaccctg cagcatatgc agcaacaatc caacctgctg ggctatctgc    360

aaaagaatac caaacaaaaa accaggaaag aaaaccacta ccaagcccac aaaaaaacca    420

accctcaaga caaccaaaaa agatcccaaa cctcaaacca ctaaatcaaa ggaagtaccc    480

accaccaagc ccacagaaga gccaaccatc aacaccacca aaacaaacat cataactaca    540

ctactcacct ccaacaccac aggaaatcca gaactcacaa gtcaaatgga aaccttccac    600

tcaacttcct ccgaaggcaa tccaagccct tctcaagtct ctacaacatc cgagtaccca    660

tcacaacctt catctccacc caacacacca cgccag                              696


<210> SEQ ID NO 4
<211> LENGTH: 298
<212> TYPE: PRT
<213> ORGANISM: Respiratory syncytial virus

<400> SEQUENCE: 4

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270
```

-continued

```
Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295


<210> SEQ ID NO 5
<211> LENGTH: 298
<212> TYPE: PRT
<213> ORGANISM: Respiratory syncytial virus

<400> SEQUENCE: 5

Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp His Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
    290                 295


<210> SEQ ID NO 6
<211> LENGTH: 292
<212> TYPE: PRT
<213> ORGANISM: Respiratory syncytial virus
```

<400> SEQUENCE: 6

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Ser Thr Tyr Leu Thr Gln Val Pro Pro
                85                  90                  95

Glu Arg Val Asn Ser Ser Lys Gln Pro Thr Thr Thr Ser Pro Ile His
            100                 105                 110

Thr Asn Ser Ala Thr Ile Ser Pro Asn Thr Lys Ser Glu Thr His His
        115                 120                 125

Thr Thr Ala Gln Thr Lys Gly Arg Ile Thr Thr Ser Thr Gln Thr Asn
    130                 135                 140

Lys Pro Ser Thr Lys Ser Arg Ser Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Met Pro Lys
    210                 215                 220

Lys Glu Ile Ile Thr Asn Pro Ala Lys Lys Pro Thr Leu Lys Thr Thr
225                 230                 235                 240

Glu Arg Asp Thr Ser Ile Ser Gln Ser Thr Val Leu Asp Thr Ile Thr
                245                 250                 255

Pro Lys Tyr Thr Ile Gln Gln Gln Ser Leu His Ser Thr Thr Ser Glu
            260                 265                 270

Asn Thr Pro Ser Ser Thr Gln Ile Pro Thr Ala Ser Glu Pro Ser Thr
        275                 280                 285

Leu Asn Pro Asn
    290
```

<210> SEQ ID NO 7
<211> LENGTH: 299
<212> TYPE: PRT
<213> ORGANISM: Respiratory syncytial virus

<400> SEQUENCE: 7

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60
```

-continued

```
Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn
    130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Thr Thr Lys
    210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
        275                 280                 285

Ser Asn Ser Thr Gln Asn Thr Gln Ser His Ala
    290                 295


<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 8

His His His His His His
1               5


<210> SEQ ID NO 9
<211> LENGTH: 23
<212> TYPE: PRT
<213> ORGANISM: Respiratory syncytial virus

<400> SEQUENCE: 9

His Phe Glu Val Phe Asn Phe Val Pro Cys Ser Ile Cys Ser Asn Asn
1               5                   10                  15

Pro Thr Cys Trp Ala Ile Cys
            20
```

RECOMBINANT RESPIRATORY SYNCYTIAL VIRUS G PROTEIN FRAGMENTS

SEQUENCE LISTING

The instant application contains a Sequence Listing which has been submitted electronically in ASCII format and is hereby incorporated by reference in its entirety. Said ASCII copy, created on Dec. 1, 2014, is named 100259.002639_SL.txt and is 15,646 bytes in size.

CROSS-REFERENCE TO RELATED APPLICATIONS

This application is based on a provisional of U.S. Ser. No. 61/910,623, filed Dec. 2, 2013, the entire contents of which are hereby incorporated by reference herein.

TECHNICAL FIELD

The present inventions relate generally to compositions and methods for vaccinations.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and worldwide conservative estimates conclude that RSV is responsible for 64 million pediatric infections and 160,000 pediatric deaths. Another unusual feature of RSV is that severe infection in infancy can be followed by years of airway dysfunction, including a predisposition to airway reactivity. RSV infection exacerbates asthma and may be involved in initiating asthma.

RSV is a member of the Paramyxoviridae family and, as such, is an enveloped virus that replicates in the cytoplasm and matures by budding through the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA, which has two overlapping open reading frames that encode two separate proteins. The 11 RSV proteins are: the RNA-binding nucleocapsid protein (N), the phosphoprotein (P), the large polymerase protein (L), the attachment glycoprotein (G), the fusion protein (F), the small hydrophobic (SH) surface glycoprotein, the internal matrix protein (M), the two non-structural proteins NS1 and NS2, and the M2-1 and M2-2 proteins encoded by the M2 mRNA. The RSV gene order is: 3'-NS1-NS2-N-P-M-SH-G-F-M2-L. Each gene is flanked by short transcription signals called the gene-start signal, present on the upstream end of the gene and involved in initiating transcription of the respective gene, and the gene-end signal, present at the downstream end of the gene and involved in directing synthesis of a polyA tail followed by release of the mRNA.

Despite a public health need for RSV vaccines, there is no licensed vaccine or effective antiviral therapy against RSV. Inactivated vaccines are not being considered for the pediatric population, as they are thought to provide little protection and can be associated with enhanced RSV disease upon subsequent natural infection. In contrast, this phenomenon of vaccine-associated enhanced disease is not observed with live-attenuated vaccines, which is likely due to differences in how the respective vaccines stimulate host immunity in RSV-naïve individuals.

The development of live-attenuated vaccines has been in progress since the 1960's but has been complicated by a number of factors. For example, RSV grows only to moderate titers in cell culture, is often present in long filaments that are difficult to purify, and can readily lose infectivity during handling. Another problem is that the magnitude of the protective immune response is roughly proportional to the extent of virus replication (and antigen production). Thus, attenuation is accompanied by a reduction in immunogenicity, and it is essential to identify a level of replication that is well tolerated yet satisfactorily immunogenic. These studies can only be done in humans, because RSV does not replicate efficiently in most experimental animals, such as rodents and monkeys. Chimpanzees are more permissive but are not readily available. Another obstacle is the difficulty in developing attenuating mutations.

Given the difficulties of developing a live-attenuated RSV vaccine, a vaccine based on a recombinantly produced RSV protein is desirable. Unfortunately, previous efforts to develop vaccines of this nature have been unsuccessful. Furthermore, these efforts have mainly focused on the RSV fusion (F) protein, as the attachment (G) protein of the virus has generally not be considered attractive for this purpose, given that most antibodies capable of neutralizing the virus target the F protein.

SUMMARY

Compositions and methods useful for producing an immune response in a subject specific for the RSV G protein are described herein. The new methods and compositions described herein are made possible by the development of a new recombinant RSV G protein fragment, which has been engineered for in vitro production and is antigenically similar to the native RSV G protein. The recombinant RSV G protein fragment is capable of inducing the production of RSV G-specific antibodies when injected into a subject. These antibodies can recognize both RSV A and RSV B strains and inhibit infection of both viruses. Accordingly, the compositions and methods described herein may be useful in protecting subjects from RSV infection via immunization or raising antibodies specific for RSV, which can in turn be used to treat RSV infection.

Described herein are recombinant polypeptide fragments of the RSV G protein. These fragments have a portion of the RSV G amino acid sequence, but also may include other amino acids or protein segments, such as an epitope tag or a protein cleavage site. In one embodiment the described recombinant polypeptide includes an amino acid sequence from the RSV G protein. In a particular embodiment the described recombinant polypeptide has an amino acid sequence from the RSV G protein that does not include amino acids from the transmembrane domain of the protein. For example, the recombinant polypeptide may have only the ectodomain sequence from the RSV G protein. In some embodiments the recombinant polypeptide contains only a subsection of the RSV G ectodomain. In one such embodiment the polypeptide described herein contains amino acids 67-298 of an RSV G protein. An example of an embodiment of a recombinant polypeptide that contains only a subsection of the RSV G ectodomain is the peptide of SEQ ID NO: 2.

In some embodiments the described polypeptides may form oligomeric compounds having at least two of the described polypeptides.

The recombinant polypeptide fragments of the RSV G protein described herein can be further modified to include additional polypeptide sequences that are useful for tracking the peptide (e.g., a peptide tag), prolonging the half-life of the peptide in vivo (e.g., adding a carrier protein or peptide), purifying the peptide (e.g., a peptide epitope), modifying the peptide after purification (e.g., a cleavage site), or enhancing the immunogenicity of the peptide (e.g., a carrier protein or peptide). For example, the described peptides could be designed to include an epitope tag, such as a polyhistidine tag. In an alternative embodiment, the described peptides could be designed to include an epitope tag and a cleavage site for removing the epitope tag.

Polynucleotide sequences encoding the described polypeptides are also provided herein. In some embodiments the polynucleotides described herein are codon optimized to facilitate improved expression in a host of interest. For example, in one embodiment the described polynucleotides are codon optimized for expression by an *E. coli* bacterium. In other embodiments the described polynucleotides are codon optimized for expression in any one of a mammalian cell, insect cell, yeast, or bacterium. In one embodiment, the polynucleotide optimized for expression by an *E. coli* bacterium has the sequence of SEQ ID NO: 1. A further embodiment of this polynucleotide consists of the sequence of SEQ ID NO: 1 and a sequence encoding a cleavage site and an epitope tag. In another embodiment, the polynucleotide is optimized for expression by a mammalian cell and has the sequence of SEQ ID NO: 3. A further embodiment of this polynucleotide consists of the sequence of SEQ ID NO: 3 and a sequence encoding a cleavage site and an epitope tag. Vectors for expressing the described polynucleotides are also included in the present disclosure. Accordingly, viral and non-viral vectors that may be used in conjunction with the described polynucleotides are described herein. In a particular embodiment, the polynucleotide sequences encoding the described polypeptides are inserted into the pSK vector to allow for expression of the polypeptide by a cell transformed with the vector.

Cells that may be used to express the polynucleotide sequences encoding the described polypeptides are also provided herein. These cells include mammalian cells, insect cells, yeast, or bacterial cells. While a number of different cell types may be used to produce the polypeptides described herein, this present disclosure makes use of *E. coli* bacteria for this purpose. Thus, *E. coli* are one example of a cell that may be used to express the polynucleotide sequences encoding the described polypeptides are also provided herein. The cells described as being suitable to express the polynucleotide sequences encoding the described polypeptides are also provided herein may be transformed with one of the vectors described herein for expressing the polypeptides disclosed herein. These expressed proteins can be refolded under controlled redox conditions in vitro to produce properly folded RSV G proteins that may display the conformational epitopes relevant for neutralization of RSV virus.

The RSV G polypeptides provided in this disclosure may be administered to a subject to generate an immune response. Thus, the disclosed polypeptides may be useful for immunizing a subject against RSV infection, or for generating antibodies specific to the RSV G protein that may be isolated and used to treat RSV infection. Accordingly, methods are provided herein for administering the described RSV G polypeptides in an amount sufficient to generate an immune response by a subject. The described methods may be carried out by administering the described peptides directly to a subject in order to cause an immune response to the peptide. Alternatively, a polynucleotide encoding one of the recombinant RSV G polypeptides described herein could be administered to a subject in order to cause expression of the polypeptide by the cells of a host, which would in turn elicit an immune response direct to the expressed polypeptide. In some embodiments the peptide, or corresponding polynucleotide, is administered with an adjuvant in order to enhance the subject's immune response against the polypeptide. These properly folded oligomeric RSV G proteins can generate antibodies that recognize conformational epitopes relevant for effective neutralization of RSV virus.

Pharmaceutical compositions of the described polypeptides and polynucleotides are also disclosed herein, in accordance with the methods provided herein for administering these polypeptides and polynucleotides to a subject to inhibit RSV infection.

BRIEF DESCRIPTION OF THE DRAWINGS

FIG. 1 shows an alignment of the full-length G protein amino acid sequence from 4 different RSV strains (A2, A-Long, B-18537, and B1). As can be seen from the alignment, there are multiple regions with conserved sequences between different strains. These conserved regions could be important for generation of cross-neutralizing antibodies.

FIG. 3(*b*) Depicts SDS-PAGE separation of chromatography fractions B6-11 (circled on the x-axis of FIG. 3(*a*)).

FIG. 7(*b*) Binding of rabbit post-vaccination sera immunized with *E. coli*-produced, denatured RSV G0-dTM protein before and after 2nd (IM2) immunization. The data shows moderate titer of binding antibodies in the post-vacciantion sera after 2nd immunization against the RSV-G protein.

FIG. 9 shows that RSV G produced in *E. coli* (REG) induces higher neutralizing antibodies than mammalian produced RSV G (RMG) with fewer immunizations in rabbits.

FIG. 14 shows that mice vaccinated with REG protein show a significantly higher antibody response compared to RMG.

FIG. 15 shows that REG protects from cytokine induction while high levels of cytokine production following RSV-A2 strain challenge in RMG (but not REG) immunized mice compared to placebo on day 2.

FIG. 16 shows RMG induces a high level of cytokine production after challenge with heterologous RSV-B1 strain compared to placebo on day 2.

FIG. 18 shows a summary of the REG and RMG vaccines.

DETAILED DESCRIPTION OF ILLUSTRATIVE EMBODIMENTS

Figure 2:
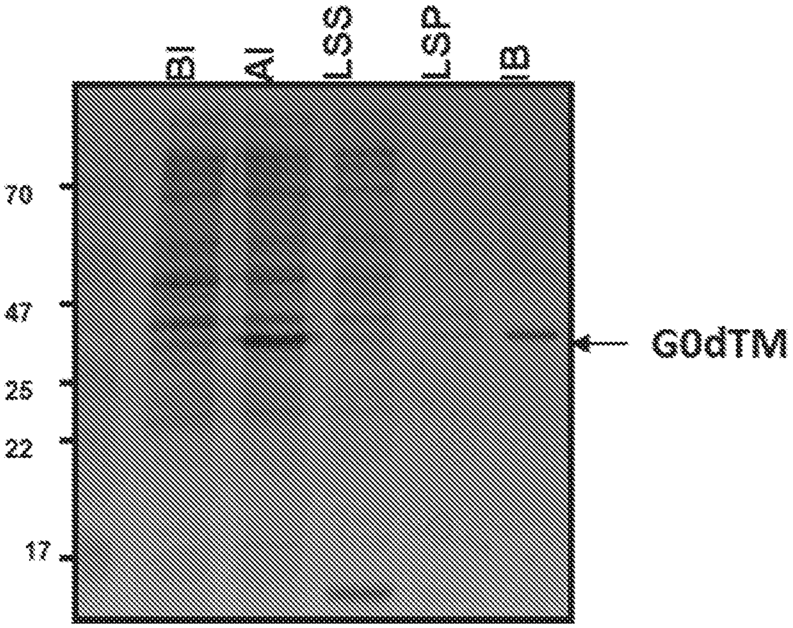
FIG. 2 Depicts a SDS-PAGE fractionation of samples from bacteria transfected with a vector encoding RSV G-dTM that were collected before induction (BI), collected after induction (AI), low speed centrifugation supernatant (LSS), low speed centrifugation pellet (LSP) and from inclusion bodies (IB). Induction of bacterial cells by IPTG clearly shows production of G0-dTM protein that was predominantly present as an insoluble protein and was isolated in inclusion bodies.

Described herein are recombinant polypeptides derived from the RSV G protein, as well as polynucleotides encoding the described proteins, as well as vectors and cells relating to the described polynucleotides. Methods of using the polypeptides and polynucleotides disclosed herein are also provided.

Various terms relating to aspects of the present description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Pharmaceutically acceptable" refers to those properties and substances which are acceptable to the patient from a pharmacological/toxicological point of view and to the manufacturing pharmaceutical chemist from a physical/chemical point of view regarding composition, formulation, stability, patient acceptance, and bioavailability.

"Pharmaceutically acceptable carrier" refers to a medium that does not interfere with the effectiveness of the biological activity of the active ingredient(s) and is not toxic to the subject to which it is administered.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

As used herein the term "polypeptide" means three or more covalently attached amino acids. The term encompasses proteins, protein fragments, and protein domains.

The term "fusion" or "fused" when used in the context of a fusion protein, or similar construct, means the covalent joining of two polypeptide products (or their corresponding polynucleotides) by genetic engineering. The fused segments may be fused directly to one another, but may also be indirectly fused to one another having interceding sequences between the segments of interest. This term is distinct form the RSV "fusion protein" which is a protein of the virus that mediates fusion with a host cell.

RSV G Polypeptide Fragments

Described herein are recombinant polypeptide fragments of the RSV G protein. These fragments have a portion of the RSV G amino acid sequence, but also may include other amino acids or protein segments, such as an epitope tag or a protein cleavage site. In one embodiment the described recombinant polypeptide includes an amino acid sequence from the RSV G protein. For example, the described recombinant polypeptide may include the complete ectodomain of the G protein but only a portion of the transmembrane domain of the G protein. In one embodiment the described recombinant polypeptide has an amino acid sequence from the RSV G protein that only includes the amino acids of the ectodomain and three amino acids from the transmembrane domain most proximal to the ectodomain of the protein. In one embodiment the described recombinant polypeptide has an amino acid sequence from the RSV G protein that only includes the amino acids of the ectodomain and two amino acids from the transmembrane domain most proximal to the ectodomain of the protein. In one embodiment the described recombinant polypeptide has an amino acid sequence from the RSV G protein that only includes the amino acids of the ectodomain and the single amino acid from the transmembrane domain most proximal to the ectodomain of the protein. In one embodiment the described recombinant polypeptide has an amino acid sequence from the RSV G protein that does not include amino acids from the transmembrane domain of the protein. For example, the recombinant polypeptide may have only the ectodomain sequence from the RSV G protein. In one such embodiment the polypeptide described herein contains from about amino acid 67 to about amino acid 298 of an RSV G protein. In one embodiment the polypeptide described herein contains from about amino acid 100 to about amino acid 298 of an RSV G protein. In one such embodiment the polypeptide described herein contains from about amino acid 130 to about amino acid 298 of an RSV G protein. In one such embodiment the polypeptide described herein contains from about amino acid 160 to about amino acid 298 of an RSV G protein. In one such embodiment the polypeptide described herein contains from about amino acid 190 to about amino acid 298 of an RSV G protein. In one such embodiment the polypeptide described herein contains from about amino acid 210 to about amino acid 298 of an RSV G protein. In one embodiment the polypeptide described herein contains amino acids 67-298 of an RSV G protein. In one embodiment the polypeptide described herein contains amino acids 68-298 of an RSV G protein. In one embodiment the polypeptide described herein contains amino acids 69-298 of an RSV G protein. In one embodiment the polypeptide described herein contains amino acids 70-298 of an RSV G protein. In one embodiment the polypeptide described herein contains amino acids 71-298 of an RSV G protein. In one embodiment the polypeptide described herein contains amino acids 72-298 of an RSV G protein. In one embodiment the polypeptide described herein contains amino acids 73-298 of an RSV G protein. In one embodiment the polypeptide described herein contains amino acids 74-298 of an RSV G protein. In one embodiment the polypeptide described herein contains amino acids 75-298 of an RSV G protein. In one embodiment the polypeptide described herein contains amino acids 76-298 of an RSV G protein. In one embodiment the polypeptide described herein contains amino acids 77-298 of an RSV G protein. In one embodiment the polypeptide described herein contains amino acids 78-298 of an RSV G protein. In one embodiment the polypeptide described herein contains amino acids 79-298 of an RSV G protein. In one embodiment the polypeptide described herein contains amino acids 80-298 of an RSV G protein. In one embodiment the polypeptide described herein contains amino acids 81-298 of an RSV G protein. In one embodiment the polypeptide described herein contains amino acids 82-298 of an RSV G protein. In one embodiment the polypeptide described herein contains amino acids 83-298 of an RSV G protein. In one embodiment the polypeptide described herein contains amino acids 84-298 of an RSV G protein. In one embodiment the polypeptide described herein contains amino acids 85-298 of an RSV G protein. In one embodiment the polypeptide described herein contains amino acids 86-298 of an RSV G protein. In one embodiment the polypeptide described herein contains amino acids 87-298 of an RSV G protein. In one embodiment the polypeptide described herein contains amino acids 88-298 of an RSV G protein. In one embodiment the polypeptide described herein contains amino acids 89-298 of an RSV G protein. In one embodiment the polypeptide described herein contains amino acids 90-298 of an RSV G protein. In one embodiment the polypeptide described herein contains amino acids 91-298 of an RSV G protein. In one embodiment the polypeptide described herein contains amino acids 92-298 of an RSV G protein. In one embodiment the polypeptide described herein contains amino acids 93-298 of an RSV G protein. In one embodiment the polypeptide described herein contains amino acids 94-298 of an RSV G protein. In one embodiment the polypeptide described herein contains amino acids 95-298 of an RSV G protein. In one embodiment the polypeptide described herein contains amino acids 96-298 of an RSV G protein. In one embodiment the polypeptide described herein contains amino acids 97-298 of an RSV G protein. In one embodiment the polypeptide described herein contains amino acids 98-298 of an RSV G protein. In one embodiment the polypeptide described herein contains amino acids 99-298 of an RSV G protein. In one embodiment the polypeptide described herein contains amino acids 100-298 of an RSV G protein. In some embodiments the recombinant polypeptide contains only a subsection of the RSV G ectodomain. An example of a particular embodiment of an RSV G recombinant polypeptide is the peptide of SEQ ID NO: 2.

Numerous subtypes and strains of RSV are known to exist, for example, RSV subtype A and subtype B, and further differentiated strains within each subtype. Furthermore, the amino acid sequence of the RSV G protein may be diverse among these subtypes and strains. Nonetheless, the described peptides should not be considered limited to a particular subtype or strain of the virus, as the G protein peptides from other RSV strains that correspond to those peptides exemplified herein are considered to be within the scope of this disclosure. Accordingly, in one embodiment the described recombinant polypeptide has an amino acid sequence corresponding to the RSV A2 G protein that only includes the corresponding amino acids of the ectodomain and three amino acids from the transmembrane domain most proximal to the ectodomain of the protein. In one embodiment the described recombinant polypeptide has an amino acid sequence corresponding to the RSV A2 G protein that only includes the corresponding amino acids of the ectodomain and two amino acids from the transmembrane domain most proximal to the ectodomain of the protein. In one embodiment the described recombinant polypeptide has an amino acid sequence corresponding to the RSV A2 G protein that only includes the corresponding amino acids of the ectodomain and the single amino acid from the transmembrane domain most proximal to the ectodomain of the protein. In one embodiment the described recombinant polypeptide has an amino acid sequence corresponding to the RSV A2 G protein that does not include amino acids from the transmembrane domain of the protein. For example, the recombinant polypeptide may have only the ectodomain sequence corresponding to the RSV A2 G protein ectodomain. In one embodiment the described recombinant polypeptide has an amino acid sequence corresponding to the RSV A2 G protein that does not include amino acids from the transmembrane domain of the protein. In one such embodiment the polypeptide described herein contains a sequence corresponding to from about amino acid 67 to about amino acid 298 of the RSV A2 G protein. In one embodiment the polypeptide described herein contains from about amino acid 100 to about amino acid 298 of the RSV A2 G protein. In one such embodiment the polypeptide described herein contains a sequence corresponding to from about amino acid 130 to about amino acid 298 of the RSV A2 G protein. In one such embodiment the polypeptide described herein contains a sequence corresponding to from about amino acid 160 to about amino acid 298 of the RSV A2 G protein. In one such embodiment the polypeptide described herein contains a sequence corresponding to from about amino acid 190 to about amino acid 298 of the RSV A2 G protein. In one such embodiment the polypeptide described herein contains a sequence corresponding to from about amino acid 210 to about amino acid 298 of the RSV A2 G protein. In one embodiment the polypeptide described herein contains a sequence corresponding to amino acids 67-298 of the RSV A2 G protein. In one embodiment the polypeptide described herein contains a sequence corresponding to amino acids 68-298 of the RSV A2 G protein. In one embodiment the polypeptide described herein contains a sequence corresponding to amino acids 69-298 the RSV A2 G protein. In one embodiment the polypeptide described herein contains a sequence corresponding to amino acids 70-298 the RSV A2 G protein. In one embodiment the polypeptide described herein contains a sequence corresponding to amino acids 71-298 the RSV A2 G protein. In one embodiment the polypeptide described herein contains a sequence corresponding to amino acids 72-298 the RSV A2 G protein. In one embodiment the polypeptide described herein contains a sequence corresponding to amino acids 73-298 the RSV A2 G protein. In one embodiment the polypeptide described herein contains a sequence corresponding to amino acids 74-298 the RSV A2 G protein. In one embodiment the polypeptide described herein contains a sequence corresponding to amino acids 75-298 the RSV A2 G protein. In one embodiment the polypeptide described herein contains a sequence corresponding to amino acids 76-298 the RSV A2 G protein. In one embodiment the polypeptide described herein contains a sequence corresponding to amino acids 77-298 the RSV A2 G protein. In one embodiment the polypeptide described herein contains a sequence corresponding to amino acids 78-298 the RSV A2 G protein. In one embodiment the polypeptide described herein contains a sequence corresponding to amino acids 79-298 the RSV A2 G protein. In one embodiment the polypeptide described herein contains a sequence corresponding to amino acids 80-298 the RSV A2 G protein. In one embodiment the polypeptide described herein contains a sequence corresponding to amino acids 81-298 the RSV A2 G protein. In one embodiment the polypeptide described herein contains a sequence corresponding to amino acids 82-298 the RSV A2 G protein. In one embodiment the polypeptide described herein contains a sequence corresponding to amino acids 83-298 the RSV A2 G protein. In one embodiment the polypeptide described herein contains a sequence corresponding to amino acids 84-298 the RSV A2 G protein. In one embodiment the polypeptide described herein contains a sequence corresponding to amino acids 85-298 the RSV A2 G protein. In one embodiment the polypeptide described herein contains a sequence corresponding to amino acids 86-298 the RSV A2 G protein. In one embodiment the polypeptide described herein contains a sequence corresponding to amino acids 87-298 the RSV A2 G protein. In one embodiment the polypeptide described herein contains a sequence corresponding to amino acids 88-298 the RSV A2 G protein. In one embodiment the polypeptide described herein contains a sequence corresponding to amino acids 89-298 the RSV A2 G protein. In one embodiment the polypeptide described herein contains a sequence corresponding to amino acids 90-298 the RSV A2 G protein. In one embodiment the polypeptide described herein contains a sequence corresponding to amino acids 91-298 the RSV A2 G protein. In one embodiment the polypeptide described herein contains a sequence corresponding to amino acids 92-298 the RSV A2 G protein. In one embodiment the polypeptide described herein contains a sequence corresponding to amino acids 93-298 the RSV A2 G protein. In one embodiment the polypeptide described herein contains a sequence corresponding to amino acids 94-298 the RSV A2 G protein. In one embodiment the polypeptide described herein contains a sequence corresponding to amino acids 95-298 the RSV A2 G protein. In one embodiment the polypeptide described herein contains a sequence corresponding to amino acids 96-298 the RSV A2 G protein. In one embodiment the polypeptide described herein contains a sequence corresponding to amino acids 97-298 the RSV A2 G protein. In one embodiment the polypeptide described herein contains a sequence corresponding to amino acids 98-298 the RSV A2 G protein. In one embodiment the polypeptide described herein contains a sequence corresponding to amino acids 99-298 the RSV A2 G protein. In one embodiment the polypeptide described herein contains a sequence corresponding to amino acids 100-298 the RSV A2 G protein. In some embodiments the recombinant polypeptide contains only a subsection of the RSV G ectodomain.

An RSV G protein has the ability to for homo-oligomers with other copies of the RSV G protein. In some instances the RSV G protein may form oligomeric compounds with other copies of the RSV G protein. The RSV G protein may also oligomerize with other copies of RSV G proteins from a different subtype or strain. In some instances the RSV G protein may form oligomeric compounds with copies of RSV G proteins from other subtypes or strains. Accordingly, the described peptides may also form oligomers. In one embodiment the at least two copies of a described recombinant polypeptide can form an oligomer. In one embodiment the at least three copies of a described recombinant polypeptide can form an oligomer. In one embodiment two copies of a described recombinant polypeptide form an oligomeric compound. In one embodiment three copies of a described recombinant polypeptide form an oligomeric compound. In one embodiment four copies of a described recombinant polypeptide form an oligomeric compound. In one embodiment five copies of a described recombinant polypeptide form an oligomeric compound. In one embodiment six copies of a described recombinant polypeptide form an oligomeric compound. In one embodiment seven copies of a described recombinant polypeptide form an oligomeric compound. In one embodiment eight copies of a described recombinant polypeptide form an oligomeric compound. In one embodiment nine copies of a described recombinant polypeptide form an oligomeric compound. In one embodiment 10 copies of a described recombinant polypeptide form an oligomeric compound. In some embodiments the copies of the described recombinant polypeptides that form the described oligomeric compound may be identical copies of a polypeptide. In some embodiments the copies of the described recombinant polypeptides that form the described oligomeric compound may be different copies of a polypeptide. For example, the different copies of a polypeptide could be derived from corresponding segments of different RSV stains or subtypes.

The recombinant polypeptide fragments of the RSV G protein described herein can be further modified to include additional polypeptide sequences that are useful for tracking the peptide (e.g., a peptide tag), prolonging the half-life of the peptide in vivo (e.g., adding a carrier protein or peptide), purifying the peptide (e.g., a peptide epitope), modifying the peptide after purification (e.g., a cleavage site), or enhancing the immunogenicity of the peptide (e.g., a carrier protein or peptide). For example, the described peptides could be designed to include an epitope tag, such as a polyhistidine tag. In an alternative embodiment, the described peptides could be designed to include an epitope tag and a cleavage site for removing the epitope tag.

Polynucleotides

Polynucleotide sequences encoding the described polypeptides are also provided herein. In some embodiments the polynucleotides described herein are codon optimized to facilitate improved expression in a host of interest. In some embodiments the described polynucleotides are codon optimized for expression in any one of a mammalian cell, insect cell, yeast, or bacterium. For example, in one embodiment the described polynucleotides are codon optimized for expression by an *E. coli* bacterium. Alternatively, in one embodiment the described polynucleotides are codon optimized for expression by a mammalian cell. In one embodiment, the polynucleotide optimized for expression by an *E. coli* bacterium has the sequence of SEQ ID NO: 1. A further embodiment of this polynucleotide consists of the sequence of SEQ ID NO: 1 and a sequence encoding a cleavage site and an epitope tag. For example, the polynucleotide optimized for expression by an *E. coli* could be arranged such that it first encodes an RSV G polypeptide, next encodes a protease cleavage site, and then encodes an epitope tag, all in a contiguous polypeptide. Alternatively, the polynucleotide optimized for expression by an *E. coli* could encode only an RSV G polypeptide followed by a protein tag, without a protease cleavage site, in one contiguous polypeptide. In one embodiment, the polynucleotide optimized for expression by an *E. coli* is arranged such that it first encodes the RSV G polypeptide of SEQ ID NO: 2, next encodes a protease cleavage site, and then encodes an epitope tag, all in a contiguous polypeptide. Alternatively, the polynucleotide optimized for expression by an *E. coli* could encode only the polypeptide of SEQ ID NO: 2 followed by a protein tag, without a protease cleavage site, in one contiguous polypeptide. In another embodiment, the polynucleotide is optimized for expression by a mammalian cell and has the sequence of SEQ ID NO: 3. A further embodiment of this polynucleotide consists of the sequence of SEQ ID NO: 3 and a sequence encoding a cleavage site and an epitope tag. For example, the polynucleotide optimized for expression by a mammalian cell could be arranged such that it first encodes an RSV G polypeptide, next encodes a protease cleavage site, and then encodes an epitope tag, all in a contiguous polypeptide. Alternatively, the polynucleotide optimized for expression by a mammalian cell could encode only an RSV G polypeptide followed by a protein tag, without a protease cleavage site, in one contiguous polypeptide. In one embodiment, the polynucleotide optimized for expression by a mammalian cell is arranged such that it first encodes the RSV G polypeptide of SEQ ID NO: 2, next encodes a protease cleavage site, and then encodes an epitope tag, all in a contiguous polypeptide. Alternatively, the polynucleotide optimized for expression by a mammalian cell could encode only the polypeptide of SEQ ID NO: 2 followed by a protein tag, without a protease cleavage site, in one contiguous polypeptide.

Vectors for expressing the described polynucleotides are also included in the present disclosure. Accordingly, viral and non-viral vectors that may be used in conjunction with the described polynucleotides are described herein. In a particular embodiment, the polynucleotide sequences encoding the described polypeptides are inserted into the pSK vector to allow for expression of the polypeptide by a bacterial cell transformed with the vector. In one embodiment the sequence of SEQ ID NO: 1 is inserted into a pSK vector to allow for expression of the polypeptide encoded by SEQ ID NO: 1 in *E. coli* bacteria. For mammalian expression vectors such as a pSec Tag vector may be used to express the described polypeptides. In a particular embodiment the pSec Tag vector is modified to incorporate a HTVL-I splice site (R) to form the pSecRTag vector, which can be used to express the described polypeptides. In some embodiments the vectors described herein may be modified to incorporate a label, such as a fluorophore or epitope tag.

Cells that may be used to express the polynucleotide sequences encoding the described polypeptides are also provided herein. These cells include mammalian cells, insect cells, yeast, or bacterial cells. While a number of different cell types may be used to produce the polypeptides described herein, this present disclosure makes use of *E. coli* bacteria for this purpose. Thus, *E. coli* are one example of a cell that may be used to express the polynucleotide sequences encoding the described polypeptides are also provided herein. The cells described as being suitable to express the polynucleotide sequences encoding the described polypeptides are also provided herein may be transformed with one of the vectors described herein for expressing the polypeptides disclosed herein. Various types of mammalian cells, yeast cells, insect cells, and bacteria suitable for protein expression are known by those skilled in the art, as a suitable expression system for each of these cell types.

Methods of Use

The RSV G polypeptides provided in this disclosure may be administered to a subject to generate an immune response. Thus, the disclosed polypeptides may be useful for immunizing a subject against RSV infection, or for generating antibodies specific to the RSV G protein that may be isolated and used to treat RSV infection. Accordingly, methods are provided herein for administering the described RSV G polypeptides in an amount sufficient to generate an immune response by a subject. For example, the described RSV G polypeptides may be administered via injection, aerosol, droplet, oral, topical or other route that causes the immune system of the subject to produce antibodies specific for the RSV G protein. In some embodiments the described polypeptides may administered to a subject at a dose of from about 0.1 μg/kg to about 100 μg/kg. In one embodiment a described polypeptide is administered to a subject at a dose of from about 0.1 μg/kg to about 0.5 μg/kg. In one embodiment a described polypeptide is administered to a subject at a dose of from about 0.6 μg/kg to about 1.0 μg/kg. In one embodiment a described polypeptide is administered to a subject at a dose of from about 1.5 μg/kg to about 5.0 μg/kg. In one embodiment a described polypeptide is administered to a subject at a dose of from about 6.0 μg/kg to about 10.0 μg/kg. In one embodiment a described polypeptide is administered to a subject at a dose of from about 11.0 μg/kg to about 20.0 μg/kg. In one embodiment a described polypeptide is administered to a subject at a dose of from about 21.0 μg/kg to about 30.0 μg/kg. In one embodiment a described polypeptide is administered to a subject at a dose of from about 31.0 μg/kg to about 40.0 μg/kg. In one embodiment a described polypeptide is administered to a subject at a dose of from about 41.0 μg/kg to about 50.0 μg/kg. In one embodiment a described polypeptide is administered to a subject at a dose of from about 51.0 μg/kg to about 60.0 μg/kg. In one embodiment a described polypeptide is administered to a subject at a dose of from about 61.0 μg/kg to about 70.0 μg/kg. In one embodiment a described polypeptide is administered to a subject at a dose of from about 71.0 μg/kg to about 80.0 μg/kg. In one embodiment a described polypeptide is administered to a subject at a dose of from about 81.0 μg/kg to about 90.0 μg/kg. In one embodiment a described polypeptide is administered to a subject at a dose of from about 91.0 μg/kg to about 100.0 μg/kg. The described methods may be carried out by administering the described peptides directly to a subject in order to cause an immune response to the peptide. Alternatively, a polynucleotide encoding one of the recombinant RSV G polypeptides described herein could be administered to a subject in order to cause expression of the polypeptide by the cells of a host, which would in turn elicit an immune response direct to the expressed polypeptide. In some embodiments the peptide, or corresponding polynucleotide, is administered with an adjuvant in order to enhance the subject's immune response against the polypeptide. As would be understood by those skilled in the art, the described peptide, or corresponding polynucleotide, may be administered more than once to "boost" a subject's immune response and provide for a more robust protection against infection by RSV. As a result of the vaccination the host becomes at least partially or completely immune to RSV infection, or resistant to developing moderate or severe RSV disease, particularly of the lower respiratory tract.

Pharmaceutical compositions of the described polypeptides and polynucleotides are also disclosed herein, in accordance with the methods provided herein for administering these polypeptides and polynucleotides to a subject to inhibit RSV infection. In some embodiments the described pharmaceutical compositions comprise a described polypeptide and a pharmaceutically acceptable carrier. In some embodiments the described pharmaceutical compositions comprise a described polypeptide oligomer and a pharmaceutically acceptable carrier. In some embodiments the described pharmaceutical compositions comprise a described polynucleotide and a pharmaceutically acceptable carrier. Other additives such as preservatives or stabilizers known to prolong the shelf life of a pharmaceutical composition may also be included with the described pharmaceutical composition, as would be understood by those skilled in the art.

Sequences of certain exemplified polypeptides and polynucleotides

RSV G0-dTM (67-298) codon optimized sequence for *E. coli*:

SEQ ID NO: 1

CATAAAGTCACCCCGACCACGGCGATTATCCAGGATGCCACCTCTCAAA
TCAAAAACACCACGCCGACGTACCTGACCCAGAATCCGCAACTGGGCAT
TTCACCGTCGAACCCGTCAGAAATCACCTCGCAGATTACCACGATCCTG
GCAAGCACCACGCCGGGTGTCAAAAGCACGCTGCAATCTACCACGGTGA
AAACCAAAAATACCACGACCACGCAGACCCAACCGAGCAAACCGACCAC
GAAACAGCGTCAAAATAAACCGCCGTCTAAACCGAACAATGATTTTCAC
TTCGAAGTGTTTAACTTCGTTCCGTGCAGTATTTGTTCCAACAATCCGA
CCTGCTGGGCCATTTGTAAACGCATCCCGAACAAAAAACCGGGCAAGAA
AACCACGACCAAACCGACGAAAAAACCGACCCTGAAAACGACCAAAAAA
GACCCGAAACCGCAGACGACCAAAAGCAAAGAAGTGCCGACGACCAAAC
CGACGGAAGAACCGACCATTAACACGACCAAAACCAATATTATCACGAC
CCTGCTGACCTCCAACACGACCGGCAATCCGGAACTGACCTCACAGATG
GAAACGTTCCATTCGACCAGCTCTGAAGGTAATCCGAGCCCGTCTCAGG
TCAGCACGACCTCCGAATACCCGAGCCAGCCGTCTTCTCCGCCGAATAC
CCCGCGTCAG

RSV G0-dTM (67-298) protein sequence:

SEQ ID NO: 2

HKVTPTTAIIQDATSQIKNTTPTYLTQNPQLGISPSNPSEITSQITTIL
ASTTPGVKSTLQSTTVKTKNTTTTQTQPSKPTTKQRQNKPPSKPNNDFH
FEVFNFVPCSICSNNPTCWAICKRIPNKKPGKKTTTKPTKKPTLKTTKK
DPKPQTTKSKEVPTTKPTEEPTINTTKTNIITTLLTSNTTGNPELTSQM
ETFHSTSSEGNPSPSQVSTTSEYPSQPSSPPNTPRQ

RSV G0-dTM (67-298) codon optimized sequence for Mammalian cells:

SEQ ID NO: 3

CACAAAGTCACACCAACAACTGCAATCATACAAGATGCAACAAGCCAGA
TCAAGAACACAACCCCAACATACCTCACCCAGAATCCTCAGCTTGGAAT
CAGTCCCTCTAATCCGTCTGAAATTACATCACAAATCACCACCATACTA
GCTTCAACAACACCAGGAGTCAAGTCAACCCTGCAATCCACAACAGTCA
AGACCAAAAACACAACAACAACTCAAACACAACCCAGCAAGCCCACCAC
AAAACAACGCCAAAACAAACCACCAAGCAAACCCAATAATGATTTTCAC

-continued

Sequences of certain exemplified polypeptides and polynucleotides

TTTGAAGTGTTCAACTTTGTACCCTGCAGCATATGCAGCAACAATCCAA
CCTGCTGGGCTATCTGCAAAAGAATACCAAACAAAAAACCAGGAAAGAA
AACCACTACCAAGCCCACAAAAAAACCAACCCTCAAGACAACCAAAAAA
GATCCCAAACCTCAAACCACTAAATCAAAGGAAGTACCCACCACCAAGC
CCACAGAAGAGCCAACCATCAACACCACCAAAACAAACATCATAACTAC
ACTACTCACCTCCAACACCACAGGAAATCCAGAACTCACAAGTCAAATG
GAAACCTTCCACTCAACTTCCTCCGAAGGCAATCCAAGCCCTTCTCAAG
TCTCTACAACATCCGAGTACCCATCACAACCTTCATCTCCACCCAACAC
ACCACGCCAG

EXAMPLES

Example 1

Design and Production of RSV G Variant (G0-dTM) Polynucleotide and Expression Vector The initial step in producing the G0-dTM construct was designing a codon-optimized polynucleotide encoding RSV G. For this a DNA sequences corresponding to a segment of the RSV-G gene of the RSV-A2 strain was designed for optimal expression in *E. coli* and the corresponding polynucleotide was chemically synthesized (SEQ ID NO: 1). A second polynucleotide, optimized for expression of the RSV-G gene of the RSV-A2 segment in mammalian cells, was also produced by an analogous process (SEQ ID NO: 3).

The vector pSK, a T7 promoter based expression vector, was selected for bacterial expression of the synthesized RSV G construct. This vector is best suited for expression in *E. coli*, as it also allows for the polypeptide to be expressed as a fusion protein with $His_6$ tag (SEQ ID NO: 8) at the C-terminus, which facilitates purification of the gene product. (See FIG. 4). Codon-optimized DNA encoding G0-dTM (67-298) of the RSV-A2 strain was cloned as NotI-PacI inserts in the pSK expression vector.

A pSecRTag vector was modified to incorporate a HTVL-I splice site (R). This vector was further modified to incorporate the NotI and Pad cloning site between the splice site and the V5-$His_6$ tag ("His6" disclosed as SEQ ID NO: 8) to facilitate cloning of a polynucleotide encoding the G0-dTM peptide using a NotI-PacI insert.

Example 2

Expression, Refolding, and Purification of RSV G0-dTM Expression

Figure 3A:
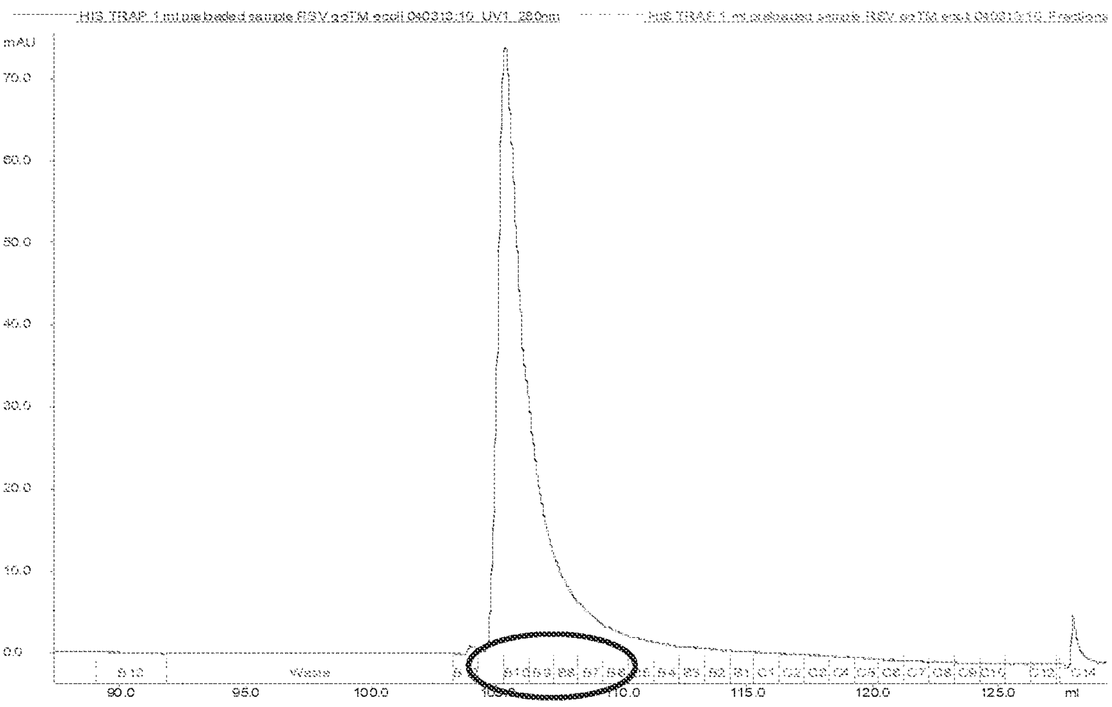
FIG. 3(*a*) Provides a chromatograph of the purification of refolded RSV G-dTM protein using His-Trap columns. Purification profile shows an intact RSV G0-dTM protein with high purity.
Figure 3B:
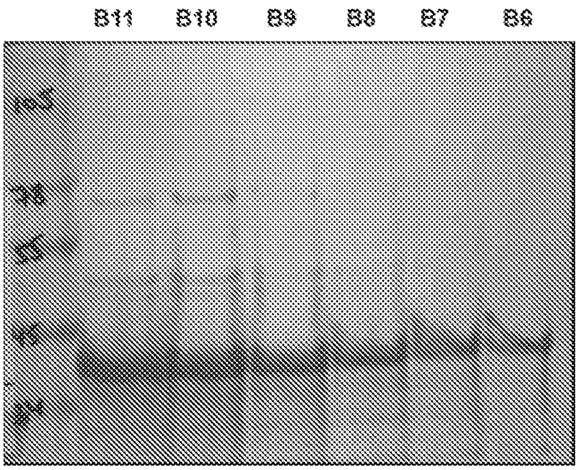

Following synthesis of the codon-optimized polynucleotide and corresponding vector, *E. coli* BL21 cells were transformed with pSK vector containing G0-dTM insert under control of T7 promoter to allow for expression of the construct. Bacterial inclusion bodies were isolated by cell lysis and multiple washing steps with 1% Triton X-100 and samples were analyzed by Coomassie staining (FIG. 3). The isolated inclusion bodies (IBs) were pelleted by centrifugation and resuspended in denaturation buffer containing 6 M guanidine hydrochloride and dithioerythreitol (DTE) at final protein concentration of 10 mg/ml. The resuspended IBs were then centrifuged to remove residual debris. For purification of G0-dTM under denaturing conditions, solubilized denatured G0-dTM was directly purified by affinity chromatography using a His binding column under reducing conditions.

For purification of native properly folded G0-dTM, the denatured supernatant was slowly diluted 100-fold in redox refolding buffer (consisting of Tris-HCl pH8, EDTA pH8, Arginine-HCl, Oxidized-Gluthatione & Reduced Glutathione) and kept at 2-8° C. for 48-72 hours. The protein solution was dialyzed against 20 mM Tris HCl pH 8.0 to remove the denaturing agents. The dialysate was filtered through a 0.45 μM filter and was subjected to purification by HisTrap™ fast flow chromatography and subjected to desalting columns and buffer exchanged to PBS pH 7.2 (FIG. 2.).

For expression in mammalian cells, plasmids encoding a secretory G0-dTM and a Flp recombinase were transfected into the human embryonic kidney cell line 293 Flp-In cell using lipofectamine 2000 reagent. Cells were grown in the fresh DMEM medium containing 150 μg/ml of hygromycin. Ten days after selection, about 40 cell clones were selected for protein expression analysis. Individual clones were expanded and maintained in DMEM with hygromycin.

For G0-dTM protein production, cells expressing G0-dTM were grown in T175 flask in serum-free medium and incubated for 24 hours. Then RSV-G0-dTM was purified from the cell supernatant by metal affinity chromatography using HisTrap columns. Fractions containing RSV-G0-dTM proteins were combined and buffer exchanged using desalting column. The expression of the G0-dTM proteins was confirmed by sodium dodecyl sulfate-polyacrylamide gel electrophoresis (SDS-PAGE) under reducing and non-reducing conditions and western blotting using anti-His antibody and G0-dTM specific sera.

Western Blot

Figure 4:
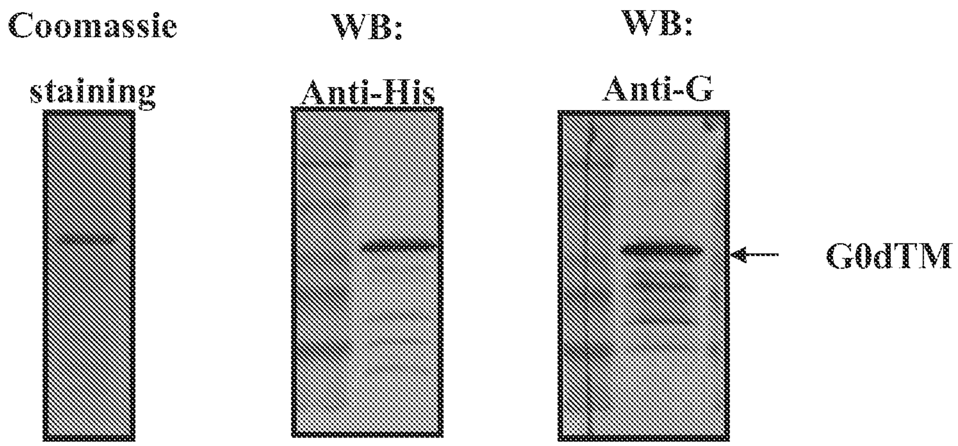
FIG. 4 Provides a characterization of bacterially produced RSV-A2 G-dTM protein using SDS-PAGE analysis, western blot with C-terminal tag (His) and RSV-G-specific antibodies.

Purified G0-dTM from the RSV A2 strain produced in mammalian cells were fractionated on a 10% SDS-PAGE gel, transferred to a PVDF membrane and immunoblotted with mouse anti-His MAb or anti RSV-G rabbit polyclonal sera. Proteins were visualized using an appropriate HRP-labeled secondary antibody followed by visualization with CN/DAB substrate (FIG. 4)

Gel Filtration Chromatography

Figure 5:
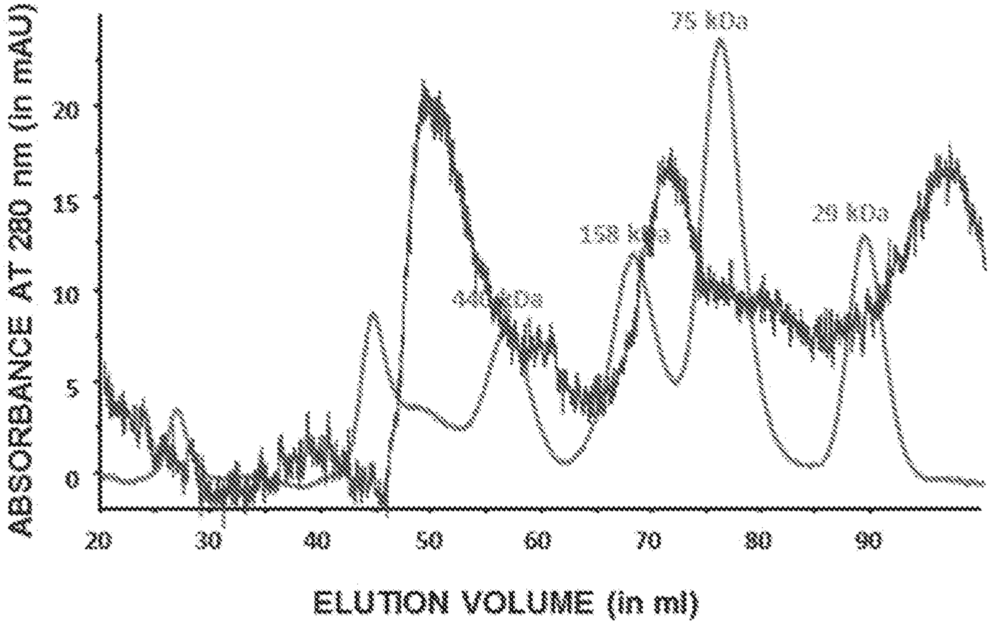
FIG. 5 depicts gel filtration chromatography of *E. coli*-produced RSV G0-dTM under controlled redox refolding conditions, which shows the presence of tetramers and higher-order oligomers similar to native RSV-G0 found on the surface of the virus particles.

Purified proteins, at a concentration of 3-5 mg/ml, were analyzed on Superdex™ S200 XK 16/60 column (GE-Healthcare) pre-equilibrated with PBS. Elution of the proteins was monitored at 280 nm. Protein molecular weight marker standards (GE healthcare) were used for column calibration and generation of standard curves, to identify the molecular weights of the test protein samples. FIG. 5 depicts a chromatograph of purified G0-dTM. The monomeric form of G0dTM is expected to have a molecular weight of approximately 28 kDa, however, the presences of higher molecular weight species indicate G0-dTM can form tetramers and higher order oligomers.

ELISA

Figure 6:
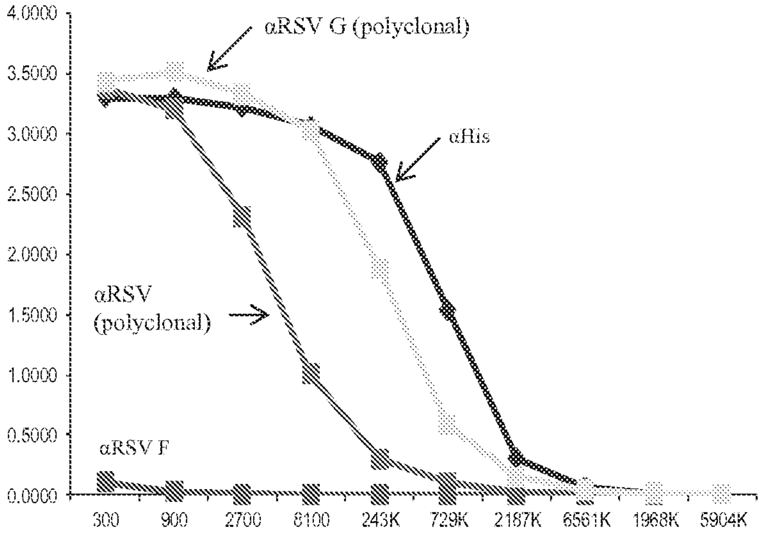
FIG. 6 shows purified G0-dTM is specifically recognized by an anti-G polyclonal sera, an anti-RSV virus sera, and an anti-His tag monoclonal antibody, while it was not recognized by anti-F1 (negative control) sera.

Immulon™ 2HB 96 well plates (Thermo Scientific) were coated with one of: *E. coli*-produced, properly folded G0-dTM, RSV G0-dTM produced in mammalian cells, or *E. coli*-produced, denatured G0-dTM at 200 ng/100 unveil and incubated overnight at 4° C. The next day the plates were incubated at room temperature (RT) for 1 hour prior to blocking with 2% whole milk/PBST (WM) for 2 hours. All primary antibodies (Mab or rabbit polyclonal sera) were diluted 1:2000 in blocking solution then added to sample and control wells and incubated for 1 hour at RT. The anti-rabbit and anti-mouse IgG conjugated HRP antibodies were diluted 1:2000 in blocking solution and incubated for 1 hour. The plates were washed 3 times with PBST in between each step and three additional times with PBS prior to adding the OPD substrate. To assess antibody binding 100 ul/well of a 1 mg/ml solution of OPD diluted in 10× stable peroxidase substrate solution was added to the plates and incubated for 10 min at RT. The reaction was stopped by adding 3.3M $H_2SO_4$ (100 ul per well) to the plates. Calormetric analysis was performed at 490 nm using a microplate reader. FIG. 6 shows that G0-dTM is bound by antibodies specific for RSV G, a histidine epitope tag, and a polyclonal sera raised against whole RSV virions; however, it is not recognized by antibodies that are specific for the RSV F protein (negative control).

Example 3

Production of RSV G-Specific Antibodies Using G0-dTM

Rabbit Immunization

Figure 7A:
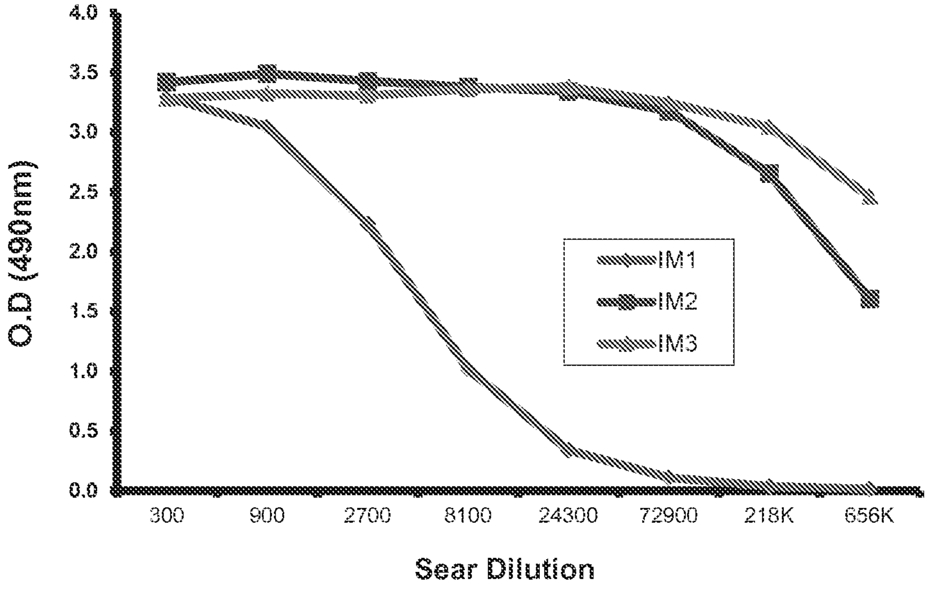
FIG. 7(*a*) shows binding of rabbit post-vaccination sera immunized with *E. coli*-produced, properly folded RSV G0-dTM protein after 1st (IM1), 2nd (IM2) and 3rd (IM3) immunization. The data shows a very high titer of binding antibodies in the post-vaccination sera—especially after 2nd and 3rd immunization against the RSV-G protein.
Figure 7B:
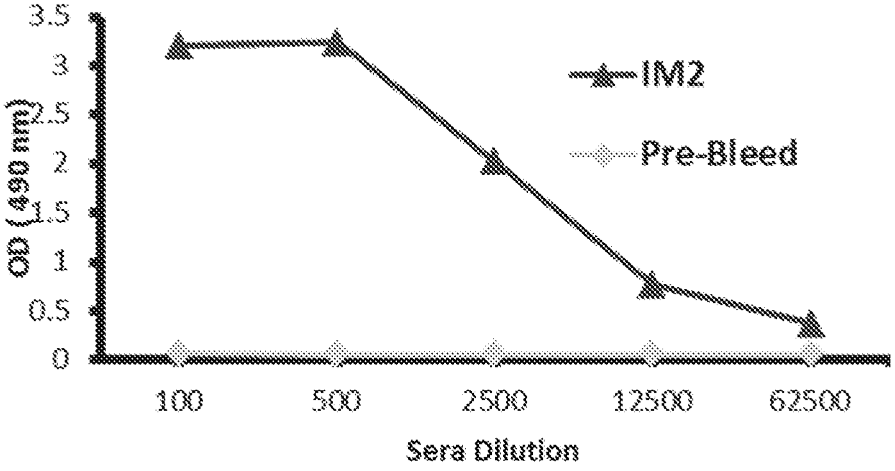

New Zealand rabbits were immunized thrice intra-muscularly at 21-days interval with 100 μg of purified RSV G0-dTM—proteins with TiterMax® adjuvant (TiterMax® Inc, Norcross, Ga., US). FIG. 7A shows the binding of rabbit post-vaccination sera immunized with *E. coli*-produced, properly folded RSV G0-dTM protein after 1st (IM1), 2nd (IM2) and 3rd (IM3) immunization against the RSV-G protein in ELISA. FIG. 7(*b*) depicst binding of rabbit post-vaccination sera immunized with *E. coli*-produced, denatured RSV G0-dTM protein before and after 2nd (IM2) immunization against the RSV-G protein.

RSV-A2 Virus Expressing-Luciferase (rA2-Rluc) Virus Titration

Virus grown in A549 cells was titrated in a luciferase assay using A549 cells. For this, virus was serially diluted 2-fold in infection media and added to cells in 24-well plates for the plaque assay or added to cells in 96-well plates for the luciferase assay. For the luciferase assay, A549 cell monolayer was incubated for 16 hours post-infection at 37° C. and 5% $CO_2$. After incubation the cells are washed twice with PBS before lysis with 20 μl per well of Renilla lysis buffer while shaking for 15 min in a Multi+ luminometer (Promega, Madison, Wis., USA). Renilla substrate (100 μl per well) was added automatically by the luminometer injector followed by a 2 second delay after substrate injection and a 2 second reading. Luminescnce measurements reported are the test sample readout divided by the readout of cells only (in the absence of virus).

RSV-Luciferase Neutralization Test (RSV-Luc-NeuT)

A549 cells were seeded at $1.6 \times 10^4$ cells in 100 μl of 10% FBS/1× Penicillin-Streptomycin/F12K medium per well in 96 well plates. Sera were heat inactivated for 30 min. at 56° C. Ten-fold diluted sera were further serially diluted 2-fold from 1:20 to 1:2560, added to rA2-Rluc virus aliquots and incubated at 37° C. for 1 hour in 5% $CO_2$. The virus-antibody mixtures were then transferred to the 96-well plates containing the cell monolayers and plates were incubated for 16 hours at 37° C. and 5% $CO_2$. The luciferase assay was performed as described above to quantify viral infection. Each serum dilution was run in duplicate, with appropriate positive and negative controls.

Luminescent readings for test samples were normalized using the A549 cells incubated with rA2-Rluc virus only (no sera added) and control values were multiplied by 100 to obtain percent of control. The percent of control values are used for linear regression analyses using the $\log_{10}$ of the reciprocal of the sera dilution on the X-axis. The trendline of the linear part of the curve is used to calculate the slope and y-intercept and 50% inhibition endpoint titers calculated using the formula: antilog of [(50+y-intercept)/slope]. Table 1 provides comparative results of this assay using the Rabbit sera immunized with properly folded *E. coli* produced RSV-G0-dTM or the *E. coli* produced denatured RSV-G0-dTM, or the mammalian system produced RSV-G0-dTM in absence or presence of Guinea Pig Complement.

Plaque Reduction Neutralization Assay (PRNT) with RSV A2 and B1 Strains

Vero cells were seeded in 24 well plates at $7\times10^4$ cells/well. Heat inactivated sera (56° C. for 30 min) were diluted 4-fold from 1:10 to 12560 in infection media (2% FBS/1× Penicillin-Streptomycin/EMEM), and were incubated at a 1:1 ratio with RSV-A2 or RSV-B1 virus diluted to yield 20-40 plaque-forming units (PFU)/50 ul in infection media containing 10% guinea pig complement (GPC). The mixture was incubated for 1 hour at 37° C. and 5% $CO_2$ prior to infection. One hundred microliters of the virus-antibody mixture was used to infect Vero cells in duplicate wells and incubated for 1 hour at 37° C. and 5% $CO_2$ before removing inoculum and adding 0.8% methylcellulose overlay. Plates were incubated for 5-7 days at 37° C. and 5% $CO_2$ before fixing the monolayer using cold 80% methanol. Plates were blocked using 2% whole milk and the plaques were visualized by immunostaining with rabbit anti-RSV F antibody at 1:2000 for 1 hour followed by goat anti rabbit IgG-alkaline phosphatase conjugated secondary antibody. Vector Black Substrate kit (Vector Laboratories, Burlingame, Calif.) was used as substrate for the alkaline phosphatase. To calculate the 50% endpoint titers the samples titers were normalized using the virus only control titers and multiplied by 100 hundred to obtain the percent of control. These values are used in a linear regression analyses using the $\log_{10}$ of the reciprocal of the sera dilution on the X-axis. The trendline of the linear part of the curve is used to calculate the slope and y-intercept and 50% inhibition endpoint titers calculated using the formula: antilog of (50+y-intercept)/slope. Table 2 provides comparative results of this assay using the sera from rabbits immunized with properly folded *E. coli* produced RSV-G0-dTM or the *E. coli* produced denatured RSV-G0-dTM, or the mammalian system produced RSV-G0-dTM against both RSV-A2 and RSV-B1 virus strains after last immunization.

TABLE 1

RSV-A2 virus neutralization titers generated following rabbit vaccination with purified RSV-G0-dTM proteins in RSV-Luc-NeuT

| | | Titer | | |
|---|---|---|---|---|
| | | −GPC | +GPC | Fold Change |
| Controls | Rb-0 | <100 | <100 | N/A |
| | RSV-1 | 1028 | 1445 | 1.4 |
| REG | IM1 | <100 | <100 | N/A |
| | IM2 | 1034 | 6015 | 5.8 |
| | IM3 | 2135 | 11533 | 5.4 |
| | IM4 | 1741 | 6644 | 3.8 |
| REG den | IM1 | <100 | <100 | N/A |
| | IM2 | <100 | 779 | N/A |
| | IM3 | 163 | 1242 | 7.6 |
| | IM4 | 334 | 2090 | 6.3 |
| RMG | IM1 | <100 | 106 | N/A |
| | IM2 | <100 | 92 | N/A |
| | IM3 | 566 | 1554 | 2.7 |
| | IM4 | 925 | 2358 | 2.6 |
| | IM5 | 731 | 1992 | 2.7 |

REG: Rabbits sera immunized with *E. coli*-produced, properly folded RSV-G0-dTM protein REG den: Rabbits sera immunized with *E. coli*-produced, denatured RSV-G0-dTM protein RMG: Rabbits sera immunized with mammalian produced RSV-G0-dTM protein GPC: 5% Guinea Pig Complement

TABLE 2

RSV-A2 & RSV-B1 virus neutralization titers generated following rabbit vaccination with purified RSV G0-dTM proteins in Plaque Reduction Neutralization Test (PRNT)

| | | RSV-PRNT | |
|---|---|---|---|
| | | A2 | B1 |
| Rb-0 | −GPC | <20 | <20 |
| | +GPC | <20 | <20 |
| RSV-1 | −GPC | 497 | 1635 |
| | +GPC | 1156 | 776 |
| REG-4 | −GPC | 583 | <20 |
| | +GPC | 12340 | 353 |
| REGden-4 | −GPC | 210 | <20 |
| | +GPC | 3015 | <20 |
| RMG-5 | −GPC | 342 | <20 |
| | +GPC | 2514 | 62 |

Rb-0: Rabbit sera before vaccination

REG-4: Rabbits sera immunized with *E. coli*-produced, properly folded RSV-G0-dTM protein after 4th vaccination REG den-4: Rabbits sera immunized with *E. coli*-produced, denatured RSV-G0-dTM protein after 4th vaccination RMG-5: Rabbits sera immunized with mammalian-produced RSV-G0-dTM protein after 5th vaccination GPC: 5% Guinea Pig Complement RSV-1 is control lot of Human sera sample A neutralization titer of >200 is considered protective against RSV

Example 4

Neutralization Data Against rRSV-G Made in *E. coli*

Surface Plasmon Resonance Test

Figure 8:
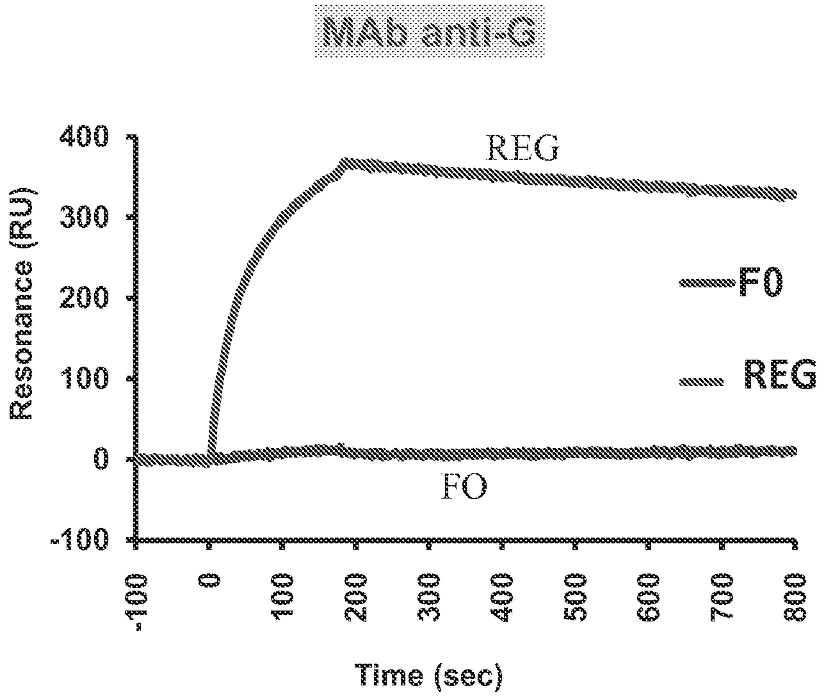
FIG. 8 shows that Anti-G MAb specifically recognizes RSV-G protein.

Steady-state binding equilibrium analysis of Anti-G neutralizing mAb 131.2G (10 μg/ml) to purified bacterially produced RSV-A2 G or RSV-F protein immobilized on a sensor chip through the free amine group, and onto a blank flow cell, free of peptide, was performed (FIG. 8). Binding was recorded using the ProteOn system surface plasmon resonance biosensor instrument (BioRad Labs, Hercules, Calif.). Similar results were obtained with two additional neutralizing anti-G mAbs (data not shown).

Neutralization Tests in Rabbits

Rabbits were immunized every four weeks with 100 μg of purified protein through intramuscular injection and blood was collected 7 days after each immunization. Sera for each immunization were tested for neutralizing antibody activity with a plaque reduction neutralization assay against a homologous (RSV-A2) and heterologous (RSV-B1) strain. Neutralization titers are reported as 50% inhibition values. RSV G produced in *E. coli* (REG) induces higher neutralizing antibodies than mammalian G (RMG) with fewer immunizations in rabbits (FIG. 9).

Figure 10:
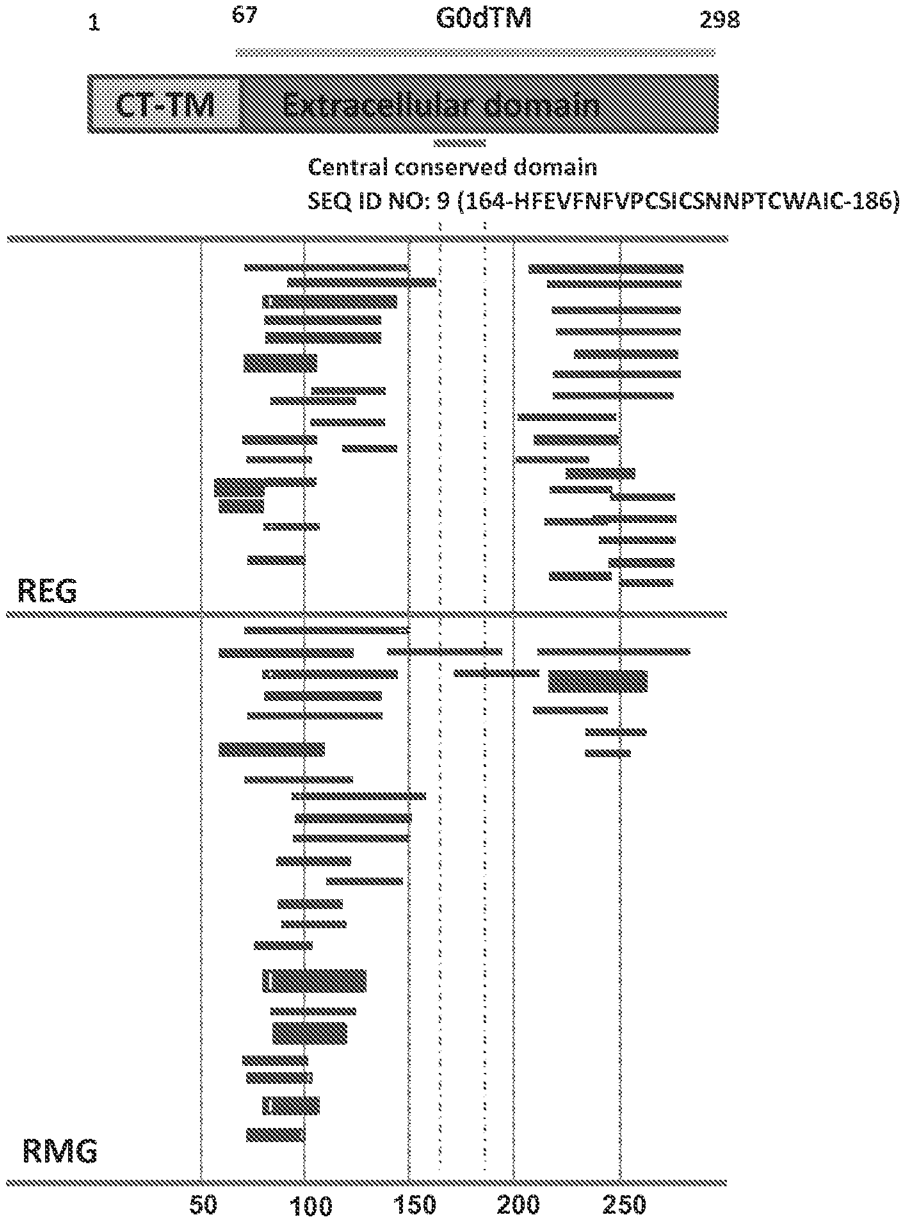
FIG. 10 shows the antibody repertoire in sera from REG or RMG immunized rabbits and that REG immunization results in a more diverse epitope repertoire. Unglycosylated G induces a wider variety of epitopes after immunization.

Analysis of the antibody epitope repertoire distribution generated in rabbit polyclonal sera following immunization with REG or RMG was performed. REG immunization results in a more diverse epitope repertoire (FIG. 10). Schematic alignment of the peptides recognized by post-vaccination sera in the rabbits, identified by panning with RSV-A2 GFPDL Amino acid designation is based on the RSV-A2 G protein sequence. Bars with arrows indicate identified inserts in the 5'-3' orientation. Only clones with frequency of >2 are shown; The diagram represents the alignment of peptides in the RSV A2 GFPD library that bound to sera from REG (top) or RMG (bottom) immunized rabbits.

Example 5

Immunization with REG Protects Mice from RSV Challenge

Figure 11:
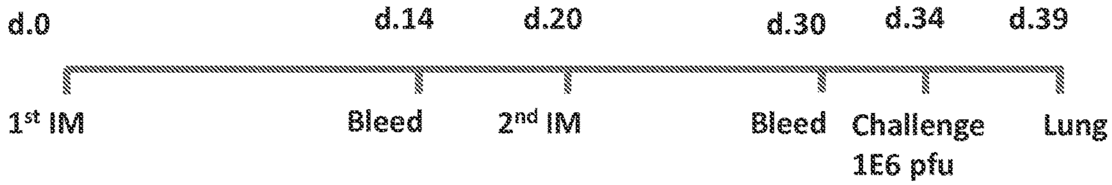
FIG. 11 shows how RSV G protein may be used as a protective vaccine.
Figure 12:
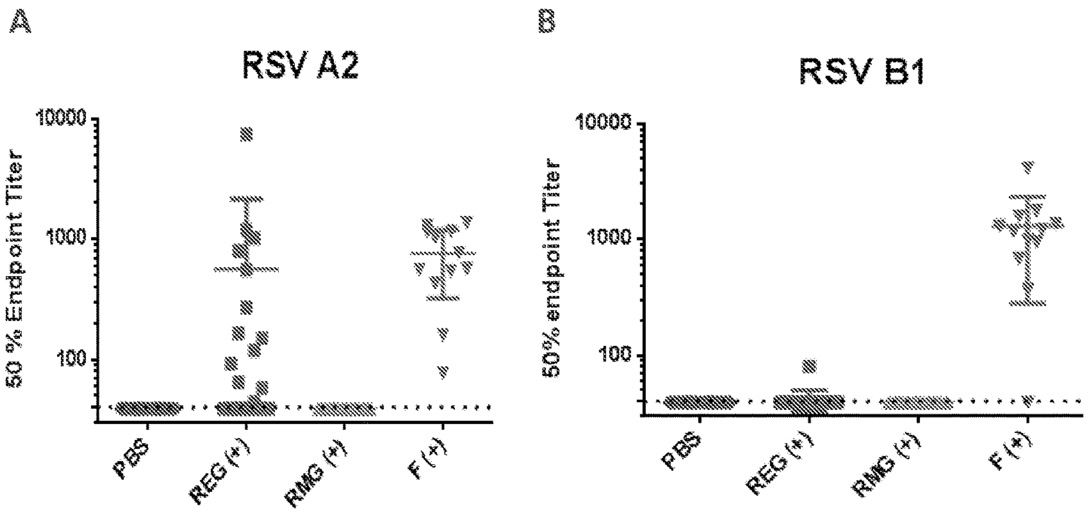
FIG. 12 shows that bacterially produced RSV G (REG) vaccine (not mammalian) protects mice against the RSV A2 and RSV B1 (heterologous) strains from lung viral loads. RSV G produced in *E. coli* (REG) immunized mice induced neutralizing antibodies against homologous but not heterologous RSV strains. F protein immunization induces cross-neutralizing antibodies.
Figure 13:
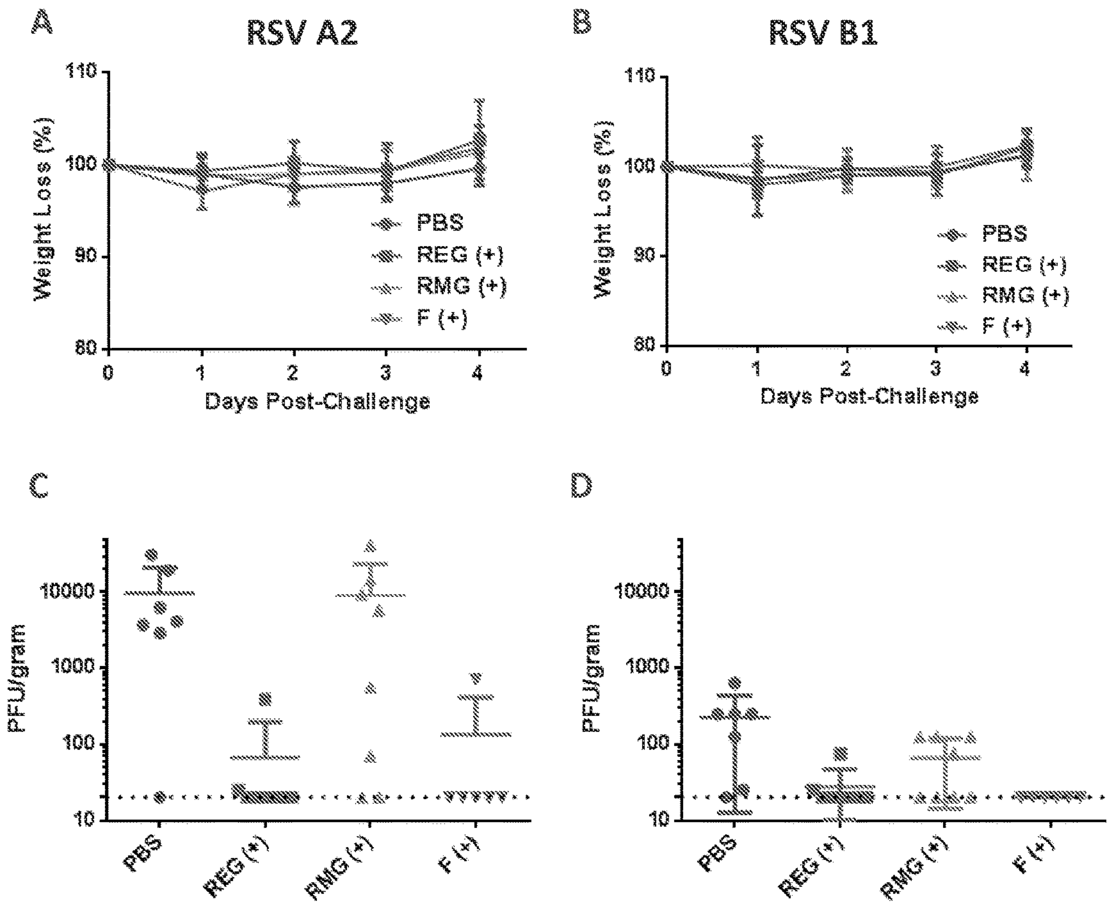
FIG. 13 shows that REG vaccine protects against both RSV-A2 and B1 virus challenge while RMG vaccine minimally protects against both RSV-A2 and B1 virus challenge.

Balb/c mice were immunized intramuscularly with PBS (placebo) or 5 μg of REG, RMG or RSV A2 F protein, with emulsigen as adjuvant, at days 0 and 20 (FIG. 11). Ten days after the second immunization blood was collected through the tail vein and sera were tested for neutralization with a plaque reduction neutralization test (FIG. 12) against a homologous RSV-A2 (FIG. 12A) or heterologous strain RSV-B1 (FIG. 12B). Neutralization is reported as 50% inhibition values. (FIG. 13). On day 34 mice were challenged intranasally with 1E6 pfu of RSV A2 (FIG. 13A and FIG. 13C) or RSV B1 (FIG. 13B and FIG. 13D). Mice were monitored for weight loss every day post challenge (FIG. 13A and FIG. 13B). Four days post challenge lungs were collected and homogenized, and lung viral titers were determined by plaque assay (FIG. 13C and FIG. 13D).

Steady-state equilibrium analysis of post-vaccination mice sera to refolded bacterially produced RSV-A2 G (*E. coli* G) or mammalian RSV-G were measured using surface plasmon resonance (SPR). Binding of the antibodies to the immobilized protein is shown as resonance units (RU) values (FIG. 14). Hundred-fold diluted individual post-vaccination sera from the three groups of the mice vaccination studies were passed over a sensor chip immobilized with *E. coli* G or mammalian RSV-G.

Cytokine Induction in Mice

High levels of cytokine production following RSV-A2 challenge in RMG (but not REG) immunized mice compared to placebo on day 2 post challenge are shown. Lung homogenates from day 2 post challenge were diluted 2-fold in infection media with a 2× concentration of protease inhibitors and used in a Bio-Plex Pro™ Mouse Cytokine 23-plex assay. Analysis of cytokine production in the lungs following homologous challenge is shown (FIG. 15). Values represent the average of three mice±standard deviation. Values underlined are >5-fold higher than the placebo (PBS) control. Values below the assay's limit of detection were assigned a value according to the minimum detection limit of the specific cytokine standard. Statistical significance was analyzed using a one-way ANOVA Tukey Post Hoc Significance Test. A p-value less than 0.05 was considered significant and represented with an * (compared to PBS) or # (compared to REG).

RMG induces a high level of cytokine production after challenge with heterologous RSV-B1 strain compared to placebo or REG on day 2 post challenge. Lung homogenates from day 2 post-RSV-B1 challenge were diluted 2-fold in infection media with 2× concentration of protease inhibitors and used in a Bio-Plex Pro™ Mouse Cytokine 23-plex assay (FIG. 16). Values represent the average of three mice±standard deviation. Values underlined are >5-fold higher than the placebo control. Values below the assay's limit of detection were assigned a value according to the minimum detection limit of the specific cytokine standard. Statistical significance was analyzed using a one-way ANOVA Tukey Post Hoc Significance Test. A p-value less than 0.05 was considered significant and represented with an * (compared to PBS) or # (compared to REG).

Figure 17:
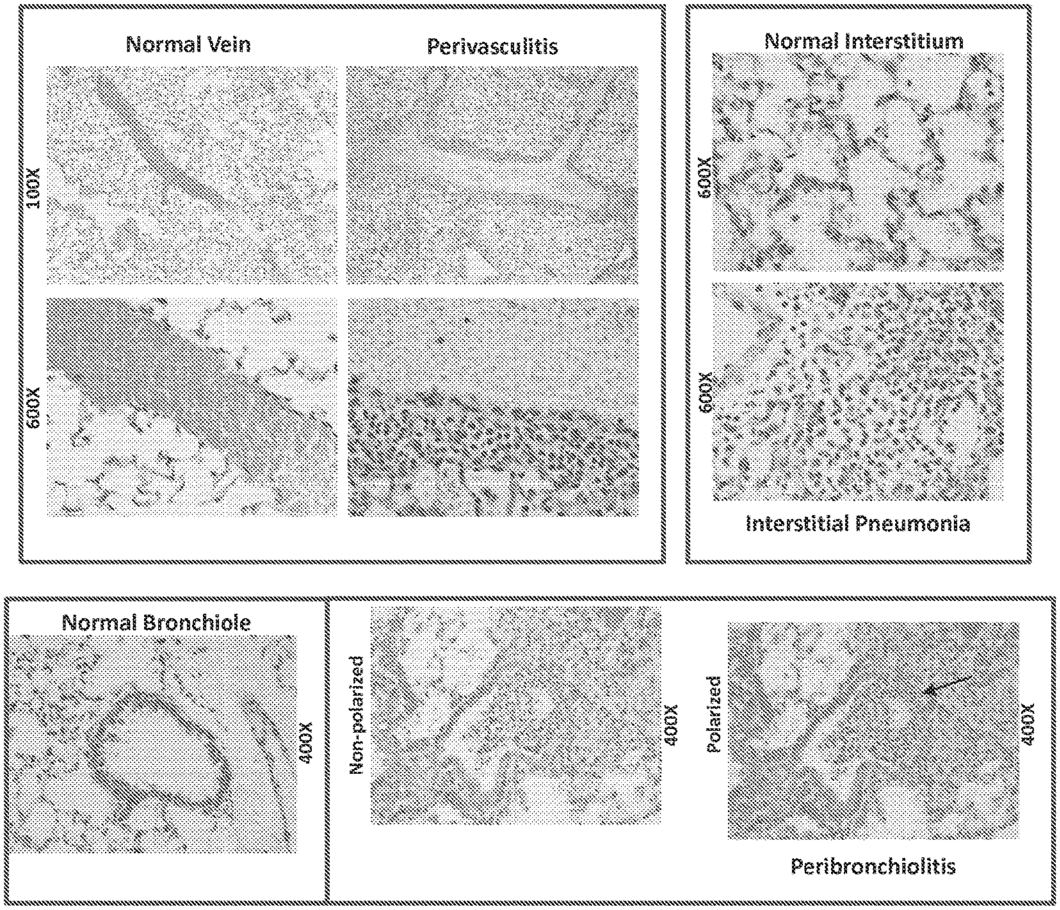
FIG. 17 shows histopathology analysis of lungs from REG and RMG immunized mice after RSV challenge. REG provides high protection from virus pathology, while RMG induces perivasculitis with eosinophilia.

Histopathology analysis of lungs from REG and RMG immunized mice after RSV challenge was performed (FIG. 17). REG provides high protection from virus pathology, while RMG induces perivasculitis with eosinophilia. Mice lungs collected on day 2 post challenge were inflated with formalin and embedded in parafilm. Sections of the lungs were mounted and stained with hematoxylin and eosin. Slides were scored depending on the severity of the observed perivasculitis, interstitial pneumonia, septal necrosis and pleuritis. A score of 0=none; 1, minimal; 2, mild; 3, moderate; 4, severe; for a maximum possible total score of 20. The table represents the average of 3 mice per group.

What is claimed:

1. A soluble unglycosylated oligomeric RSV G ectodomain.

2. The soluble unglycosylated oligomeric RSV G ectodomain of claim 1, comprising the amino acid sequence of SEQ ID NO: 2.

3. A method of generating an immune response to RSV G in a subject, comprising administering to the subject the soluble unglycosylated oligomeric RSV G ectodomain of claim 1 in an amount sufficient to elicit an immune response by the subject.

4. The method of claim 3, wherein the amount of the soluble unglycosylated oligomeric RSV G ectodomain sufficient to elicit the immune response is a dose of from 0.1 μg/kg to 100 μg/ kg.

5. The method of claim 3, wherein the soluble unglycosylated oligomeric RSV G ectodomain is also administered with an adjuvant.

6. A pharmaceutical composition comprising the soluble unglycosylated oligomeric RSV G ectodomain of claim 1.

7. The soluble unglycosylated oligomeric RSV G ectodomain of claim 1 comprising at least two RSV G ectodomains.

8. The soluble unglycosylated oligomeric RSV G ectodomain of claim 1 comprising four RSV G ectodomains.

9. The pharmaceutical composition of claim 6, wherein the RSV G ectodomain forms a homo-oligomer comprising at least two RSV G ectodomains.

10. The pharmaceutical composition of claim 9, wherein the homo-oligomer comprises four RSV G ectodomains.

11. The pharmaceutical composition of claim 6, further comprising an adjuvant.

12. The method of claim 3, wherein the RSV G ectodomain comprises the amino acid sequence of SEQ ID NO: 2.

13. The method of claim 3, wherein the ectodomain forms a homo-oligomer comprising at least two RSV G ectodomains.

14. The method of claim 13, wherein the homo-oligomer comprises four RSV G ectodomains.

15. A method of producing the soluble unglycosylated oligomeric RSV G ectodomain of claim 1, comprising the steps of:

expressing a nucleic acid molecule encoding an RSV G ectodomain in bacterial cells;

lysing the bacterial cells and purifying bacterial inclusion bodies from the lysed cells;

resuspending the bacterial inclusion bodies in protein denaturation buffer to denature protein in the inclusion bodies;

processing the denatured protein under redox refolding conditions to provide refolded protein;

purifying RSV G ectodomain from the refolded protein, wherein the purified RSV G ectodomain is soluble, unglycosylated, and oligomeric, thereby producing the soluble unglycosylated oligomeric RSV G ectodomain.

16. The soluble unglycosylated oligomeric RSV G ectodomain produced by the method of claim 15.

17. The method of claim 15, wherein the nucleic acid molecule encodes the amino acid sequence of SEQ ID NO: 2.

18. The method of claim 17, wherein the nucleic acid molecules comprises the nucleic acid sequence of SEQ ID NO: 1.

* * * * *